US008551779B2

(12) United States Patent
Hald et al.

(10) Patent No.: US 8,551,779 B2
(45) Date of Patent: Oct. 8, 2013

(54) DDR1-MEDIATED CELL PURIFICATION OF PANCREATIC ENDOCRINE CELLS THROUGH THEIR PROGENITORS

(75) Inventors: Jacob Hald, Birkerød (DK); Ole Dragsbæk Madsen, Søborg (DK); Palle Serup, København Ø (DK)

(73) Assignee: Novo Nordisk A/S, Bagsvaerd (DK)

( * ) Notice: Subject to any disclaimer, the term of this patent is extended or adjusted under 35 U.S.C. 154(b) by 295 days.

(21) Appl. No.: 12/810,960

(22) PCT Filed: Dec. 19, 2008

(86) PCT No.: PCT/EP2008/068061
§ 371 (c)(1),
(2), (4) Date: Sep. 8, 2010

(87) PCT Pub. No.: WO2009/083502
PCT Pub. Date: Jul. 9, 2009

(65) Prior Publication Data
US 2011/0014160 A1    Jan. 20, 2011

Related U.S. Application Data

(60) Provisional application No. 61/009,979, filed on Jan. 3, 2008.

(30) Foreign Application Priority Data

Dec. 28, 2007    (EP) ..................................... 07124132

(51) Int. Cl.
*C12N 5/08*    (2006.01)
(52) U.S. Cl.
USPC .......................................... 435/366; 435/377
(58) Field of Classification Search
USPC ................................................. 435/366, 377
See application file for complete search history.

(56) References Cited

U.S. PATENT DOCUMENTS

| | | | |
|---|---|---|---|
| 6,242,666 B1 * | 6/2001 | Sarvetnick et al. | 800/18 |
| 6,436,704 B1 * | 8/2002 | Roberts et al. | 435/366 |
| 2006/0014808 A1 | 1/2006 | Hughes et al. | |
| 2006/0148081 A1 | 7/2006 | Kelly et al. | |
| 2006/0205072 A1 | 9/2006 | Uchida et al. | |
| 2008/0242594 A1 | 10/2008 | McKay et al. | |
| 2011/0020297 A1 * | 1/2011 | Hald et al. | 424/93.7 |
| 2011/0286977 A1 | 11/2011 | Roep et al. | |
| 2011/0287011 A1 * | 11/2011 | Gurney et al. | 424/139.1 |

FOREIGN PATENT DOCUMENTS

| | | |
|---|---|---|
| CA | 2600568 A1 | 9/2006 |
| WO | 01/57190 A2 | 8/2001 |
| WO | 02/74946 A2 | 9/2002 |
| WO | 2004/001008 A2 | 12/2003 |
| WO | 2004/093804 A2 | 11/2004 |
| WO | 2005/030032 A2 | 4/2005 |
| WO | WO 2005/063971 | 7/2005 |
| WO | 2005/113596 A2 | 12/2005 |
| WO | WO 2005/116073 | 12/2005 |
| WO | 2006/023209 A2 | 3/2006 |
| WO | 2006/025028 A2 | 3/2006 |
| WO | 2006/054305 A2 | 5/2006 |
| WO | 2007/103282 A2 | 9/2007 |
| WO | 2009/083502 A1 | 7/2009 |

OTHER PUBLICATIONS

Sakamoto O. et al. Expression of Discoidin Domain Receptor 1 Tyrosine Kinase on the Human Bronchial Epithelium. European Respiratory J 17(5)969-974, May 2001.*
D'Amour K. et al. Production of Pancreatic Hormone Expressing Endocrine Cells from Human Embryonic Stem Cells. Nature Biotechnology 24(11)1392-1401, Oct. 19, 2006.*
Jorgensen M. et al. An Illustrated Review of Early Pancreas Development in the Mouse. Endocrine Reviews 28(6)685-705, Oct. 2007.*
Ram, Rosalyn et al., Journal of Neuro-Oncology, "Discoidin Domain Receptor-1A (DDR1A) Promotes Glioma Cell Invasion and Adhesion in Association With Matrix Metallopreteinase-2", 2006, vol. 76, No. 3, pp. 239-248.
Cirulli et al., Journal of Cell Biology, 1998, vol. 140, pp. 1519-1534.
Circulli et al, Journal of Cell Biology, 2000, vol. 150, pp. 1445-1460.
Ahnfelt-Ronne, J. et al., BMC Developmental Biology, Biomed Central Ltd., London, 2007, vol. 7, No. 1, p. 63.
Apelqvist, A. et al., Nature, 1999, vol. 400, No. 6747, pp. 877-881.
Eiraku, M. et al., Journal of Biological Chemistry, 2002, vol. 277, No. 28, pp. 25400-25407.
Hald et al., Journal of Histochemistry and Cytochemistry, 2008, vol. 56, No. 6, pp. 587-595.
Sugiyama, T. et al., Proceedings of the National Academy of Sciences of the USA, 2007, vol. 104, No. 1, pp. 175-180.
White, P. et al., Diabetes, 2008, vol. 57, No. 3, pp. 654-668.
Xu, X. et al., Cell, 2008, vol. 132, No. 2, pp. 197-207.
Banerjee et al., "A Simple Two-Step Protocol for the Purification of Human Pancreatic Beta Cells", Diabetologia, 2009, vol. 52, pp. 621-625.
Krijger et al., "Enrichment of Beta Cells From the Human Fetal Pancreas by Fluorescence Activated Cell Sorting With a New Monoclonal Antibody", Diabetologia, 1992, vol. 35, pp. 436-443.
Dorrell et al., "Isolatio of Major Pancreatic Cell Types and Long-Term Culture-Initiating Cells Using Novel Human Surface Markers", Stem Cell Research, 2008, vol. 1, pp. 183-194.

(Continued)

*Primary Examiner* — Ralph Gitomer
(74) *Attorney, Agent, or Firm* — Jianjie Hu

(57) ABSTRACT

The invention relates to a method of identifying, obtaining and/or quantifying a culture of pancreatic cells selected from the group consisting of ductal/endocrine progenitor cells, endocrine progenitor cells, early endocrine cells, and fully differentiated endocrine cells. Also contemplated is a method of expanding the numbers of such cells as well as sorting such cells. The invention further relates to a selective cell surface marker, DDR1, that permits the selection of a unique subset of cells with pancreatic endocrine progenitor phenotype. Furthermore, the invention relates to isolated cells selected from such cells and compositions thereof.

17 Claims, 5 Drawing Sheets

(56) References Cited

OTHER PUBLICATIONS

Hori et al, "Enrichment of Putative Pancreatic Progenitor Cells From Mice by Sorting for Prominin1 (CD133) and Platelet-Derived Growth Factor Receptor β", Stem Cells, 2008, vol. 26, pp. 2912-2920.
Iglesias et al., "Comprehensive Analysis of Human Pancreatic Islets Using Flow and Laser Scanning Cytometry", Transplantation Proceedings, 2008, vol. 40, pp. 351-354.
Koblas et al., "Differentiation of CD133-Positive Pancreatic Cells Into Insulin-Producing Islet-Like Cell Clusters", Transplantation Proceedings, 2008, vol. 40, pp. 415-418.
Martin et al., "Cloning and Characterization of the Human and Rat Islet-Specific Glucose-6-Phosphatase Catalytic Subunit-Related Protein (IGRP) Genes", Journal of Biological Chemistry, 2001, vol. 276, No. 27, pp. 25197-25207.
Vissing et al., "Monoclonal Antibodies Against Pancreatic Islet-Cell-Surface Antigens Selected by Flow Cytofluorometry", Scandinavian Journal Immunology, 1986, vol. 23, pp. 425-433.
NCBI webpage for G6PC2, downloaded from NCBI at http://www.ncbi.nlm.nih.gov/gene/57818 accessed Jul. 11, 2013.
Katoh, M et al. International Journal of Oncology. "Notch Signaling in Gastrointestinal Tract (Review)." 2007. vol. 30(1). pp. 247-251.
Mukherjee R et al. Journal of Immunology. "Identification of CD4+ T Cell Specific Epitopes of ISLET-Specific Glucose 6 Phosphatase Catalytic Subunit Related Protein: A Novel B Cell Autoantigen in Type 1 Diabetes." 2005. vol. 174(9). pp. 5306-5315.
Jarchum I et al. Clinical Immunology. "Identification of Novel IGRP Epitopes Targeted in Type 1 Diabetes Patients." 2008. vol. 127. pp. 359-365.
Han B et al. Nature Medicine. "Prevention of Diabetes by Manipulation of Anti-IGRP Autoimmunity: High Efficiency of a Low-Affinity Peptide." 2005. vol. 11. pp. 645-652.
Ebert D et al. Diabetes. "Structure and Promoter Activity of an I S L E T—S P E C I FIC Glucose-6-Phosphatase Catalytic Subunit-Related Gene." 1999. vol. 48(3). pp. 543-551.
Dogra R et al. Diabetologia. "Alternative Splicing of G6PC2, The Gene Coding for the ISLET-Specific Glucose-6-Phosphatase Catalytic Subunit-Related Protein (IGRP), Results in Differential Expression in Human Thymus and Spleen . . ." 2006. vol. 49(5). pp. 953-957.
Arden, S D et al. Diabetes. "Molecular Cloning of a Pancreatic ISLET-Specific Glucose-6-Phosphatase Catalytic Subunit-Related Protein." 1999. vol. 48. pp. 531-542.

* cited by examiner

```
Human_isoB    MGPEALSSLLLLLLVASGDADMKGHFDPAKCRYALGMQDRTIPDSDISASSSWSDSTAAR 60
Human_isoC    MGPEALSSLLLLLLVASGDADMKGHFDPAKCRYALGMQDRTIPDSDISASSSWSDSTAAR 60
Human_isoA    MGPEALSSLLLLLLVASGDADMKGHFDPAKCRYALGMQDRTIPDSDISASSSWSDSTAAR 60
              ************************************************************

Human_isoB    HSRLESSDGDGAWCPAGSVFPKEEEYLQVDLQRLHLVALVGTQGRHAGGLGKEFSRSYRL 120
Human_isoC    HSRLESSDGDGAWCPAGSVFPKEEEYLQVDLQRLHLVALVGTQGRHAGGLGKEFSRSYRL 120
Human_isoA    HSRLESSDGDGAWCPAGSVFPKEEEYLQVDLQRLHLVALVGTQGRHAGGLGKEFSRSYRL 120
              ************************************************************

Human_isoB    RYSRDGRRWMGWKDRWGQEVISGNEDPEGVVLKDLGPPMVARLVRFYPRADRVMSVCLRV 180
Human_isoC    RYSRDGRRWMGWKDRWGQEVISGNEDPEGVVLKDLGPPMVARLVRFYPRADRVMSVCLRV 180
Human_isoA    RYSRDGRRWMGWKDRWGQEVISGNEDPEGVVLKDLGPPMVARLVRFYPRADRVMSVCLRV 180
              ************************************************************

Human_isoB    ELYGCLWRDGLLSYTAPVGQTMYLSEAVYLNDSTYDGHTVGGLQYGGLGQLADGVVGLDD 240
Human_isoC    ELYGCLWRDGLLSYTAPVGQTMYLSEAVYLNDSTYDGHTVGGLQYGGLGQLADGVVGLDD 240
Human_isoA    ELYGCLWRDGLLSYTAPVGQTMYLSEAVYLNDSTYDGHTVGGLQYGGLGQLADGVVGLDD 240
              ************************************************************

Human_isoB    FRKSQELRVWPGYDYVGWSNHSFSSGYVEMEFEFDRLRAFQAMQVHCNNMHTLGARLPGG 300
Human_isoC    FRKSQELRVWPGYDYVGWSNHSFSSGYVEMEFEFDRLRAFQAMQVHCNNMHTLGARLPGG 300
Human_isoA    FRKSQELRVWPGYDYVGWSNHSFSSGYVEMEFEFDRLRAFQAMQVHCNNMHTLGARLPGG 300
              ************************************************************

Human_isoB    VECRFRRGPAMAWEGEPMRHNLGGNLGDPRARAVSVPLGGRVARFLQCRFLFAGPWLLFS 360
Human_isoC    VECRFRRGPAMAWEGEPMRHNLGGNLGDPRARAVSVPLGGRVARFLQCRFLFAGPWLLFS 360
Human_isoA    VECRFRRGPAMAWEGEPMRHNLGGNLGDPRARAVSVPLGGRVARFLQCRFLFAGPWLLFS 360
              ************************************************************

Human_isoB    EISFISDVVNNSSPALGGTFPPAPWWPPGPPPTNFSSLELEPRGQQPVAKAEGSPTAILI 420
Human_isoC    EISFISDVVNNSSPALGGTFPPAPWWPPGPPPTNFSSLELEPRGQQPVAKAEGSPTAILI 420
Human_isoA    EISFISDVVNNSSPALGGTFPPAPWWPPGPPPTNFSSLELEPRGQQPVAKAEGSPTAILI 420
              ************************************************************

Human_isoB    GCLVAIILLLLLIIALMLWRLHWRRLLSKAERRVLEEELTVHLSVPGDTILINNRPGPRE 480
Human_isoC    GCLVAIILLLLLIIALMLWRLHWRRLLSKAERRVLEEELTVHLSVPGDTILINNRPGPRE 480
Human_isoA    GCLVAIILLLLLIIALMLWRLHWRRLLSKAERRVLEEELTVHLSVPGDTILINNRPGPRE 480
              ************************************************************

Human_isoB    PPPYQEPRPRGNPPHSAPCVPNGS------------------------------------ 504
Human_isoC    PPPYQEPRPRGNPPHSAPCVPNGSALLLSNPAYRLLLATYARPPRGPGPPTPAWAKPTNT 540
Human_isoA    PPPYQEPRPRGNPPHSAPCVPNGSALLLSNPAYRLLLATYARPPRGPGPPTPAWAKPTNT 540
              ***********************

Human_isoB    -AYSGDYMEPEKPGAPLLPPPPQNSVPHYAEADIVTLQGVTGGNTYAVPALPPGAVGDGP 563
Human_isoC    QAYSGDYMEPEKPGAPLLPPPPQNSVPHYAEADIVTLQGVTGGNTYAVPALPPGAVGDGP 600
Human_isoA    QAYSGDYMEPEKPGAPLLPPPPQNSVPHYAEADIVTLQGVTGGNTYAVPALPPGAVGDGP 600
               ***********************************************************

Human_isoB    PRVDFPRSRLRFKEKLGEGQFGEVHLCEVDSPQDLVSLDFPLNVRKGHPLLVAVKILRPD 623
Human_isoC    PRVDFPRSRLRFKEKLGEGQFGEVHLCEVDSPQDLVSLDFPLNVRKGHPLLVAVKILRPD 660
Human_isoA    PRVDFPRSRLRFKEKLGEGQFGEVHLCEVDSPQDLVSLDFPLNVRKGHPLLVAVKILRPD 660
              ************************************************************

Human_isoB    ATKNA------RNDFLKEVKIMSRLKDPNIIRLLGVCVQDDPLCMITDYMENGDLNQFLS 677
Human_isoC    ATKNASFSLFSRNDFLKEVKIMSRLKDPNIIRLLGVCVQDDPLCMITDYMENGDLNQFLS 720
Human_isoA    ATKNA------RNDFLKEVKIMSRLKDPNIIRLLGVCVQDDPLCMITDYMENGDLNQFLS 714
              *****       ************************************************

Human_isoB    AHQLEDKAAEGAPGDGQAAQGPTISYPMLLHVAAQIASGMRYLATLNFVHRDLATRNCLV 737
Human_isoC    AHQLEDKAAEGAPGDGQAAQGPTISYPMLLHVAAQIASGMRYLATLNFVHRDLATRNCLV 780
Human_isoA    AHQLEDKAAEGAPGDGQAAQGPTISYPMLLHVAAQIASGMRYLATLNFVHRDLATRNCLV 774
              ************************************************************
```

Fig. 1A

```
Human_isoB    GENFTIKIADFGMSRNLYAGDYYRVQGRAVLPIRWMAWECILMGKFTTASDVWAFGVTLW  797
Human_isoC    GENFTIKIADFGMSRNLYAGDYYRVQGRAVLPIRWMAWECILMGKFTTASDVWAFGVTLW  840
Human_isoA    GENFTIKIADFGMSRNLYAGDYYRVQGRAVLPIRWMAWECILMGKFTTASDVWAFGVTLW  834
              ************************************************************

Human_isoB    EVLMLCRAQPFGQLTDEQVIENAGEFFRDQGRQVYLSRPPACPQGLYELMLRCWSRESEQ  857
Human_isoC    EVLMLCRAQPFGQLTDEQVIENAGEFFRDQGRQVYLSRPPACPQGLYELMLRCWSRESEQ  900
Human_isoA    EVLMLCRAQPFGQLTDEQVIENAGEFFRDQGRQVYLSRPPACPQGLYELMLRCWSRESEQ  894
              ************************************************************

Human_isoB    RPPFSQLHRFLAEDALNTV  876
Human_isoC    RPPFSQLHRFLAEDALNTV  919
Human_isoA    RPPFSQLHRFLAEDALNTV  913
              *******************
```

Fig. 1B

```
Mouse_iso1      MGTGTLSSLLLLLLLVTIGDADMKGHFDPAKCRYALGMQDRTIPDSDISVSSSWSDSTAA 60
Mouse_iso2      MGTGTLSSLLLLLLLVTIGDADMKGHFDPAKCRYALGMQDRTIPDSDISVSSSWSDSTAA 60
                ************************************************************

Mouse_iso1      RHSRLESSDGDGAWCPAGPVFPKEEEYLQVDLRRLHLVALVGTQGRHAGGLGKEFSRSYR 120
Mouse_iso2      RHSRLESSDGDGAWCPAGPVFPKEEEYLQVDLRRLHLVALVGTQGRHAGGLGKEFSRSYR 120
                ************************************************************

Mouse_iso1      LRYSRDGRRWMDWKDRWGQEVISGNEDPGGVVLKDLGPPMVARLVRFYPRADRVMSVCLR 180
Mouse_iso2      LRYSRDGRRWMDWKDRWGQEVISGNEDPGGVVLKDLGPPMVARLVRFYPRADRVMSVCLR 180
                ************************************************************

Mouse_iso1      VELYGCLWRDGLLSYTAPVGQTMQLSEVMVHLNDSTYDGYTAGGLQYGGLGQLADGVVGL 240
Mouse_iso2      VELYGCLWRDGLLSYTAPVGQTMQLSEVMVHLNDSTYDGYTAGGLQYGGLGQLADGVVGL 240
                ************************************************************

Mouse_iso1      DDFRQSQELRVWPGYDYVGWSNQSFPTGYVEMEFEFDRLRTFQTMQVHCNNMHTLGARLP 300
Mouse_iso2      DDFRQSQELRVWPGYDYVGWSNQSFPTGYVEMEFEFDRLRTFQTMQVHCNNMHTLGARLP 300
                ************************************************************

Mouse_iso1      GGVECRFKRGPAMAWEGEPVRHALGGSLGDPRARAISVPLGGHVGRFLQCRFLFAGPWLL 360
Mouse_iso2      GGVECRFKRGPAMAWEGEPVRHALGGSLGDPRARAISVPLGGHVGRFLQCRFLFAGPWLL 360
                ************************************************************

Mouse_iso1      FSEISFISDVVNDSSDTFPPAPWWPPGPPPTNFSSLELEPRGQQPVAKAEGSPTAILIGC 420
Mouse_iso2      FSEISFISDVVNDSSDTFPPAPWWPPGPPPTNFSSLELEPRGQQPVAKAEGSPTAILIGC 420
                ************************************************************

Mouse_iso1      LVAIILLLLLIIALMLWRLHWRRLLSKAERRVLEEELTVHLSVPGDTILINNRPGPREPP 480
Mouse_iso2      LVAIILLLLLIIALMLWRLHWRRLLSKAERRVLEEELTVHLSVPGDTILINNRPGPREPP 480
                ************************************************************

Mouse_iso1      PYQEPRPRGTPPHSAPCVPNGSALLLSNPAYRLLLATYARPPRGPGPPTPAWAKPTNTQA 540
Mouse_iso2      PYQEPRPRGTPPHSAPCVPNGS-------------------------------------A 503
                **********************                                    *

Mouse_iso1      CSGDYMEPEKPGAPLLPPPPQNSVPHYAEADIVTLQGVTGGNTYAVPALPPGAVGDGPPR 600
Mouse_iso2      CSGDYMEPEKPGAPLLPPPPQNSVPHYAEADIVTLQGVTGGNTYAVPALPPGAVGDGPPR 563
                ************************************************************

Mouse_iso1      VDFPRSRLRFKEKLGEGQFGEVHLCEVEDPQDLVSSDFPISVHKGHPLLVAVKILRPDAT 660
Mouse_iso2      VDFPRSRLRFKEKLGEGQFGEVHLCEVEDPQDLVSSDFPISVHKGHPLLVAVKILRPDAT 623
                ************************************************************

Mouse_iso1      KNARNDFLKEVKIMSRLKDPNIIRLLGVCVQDDPLCMITDYMENGDLNQFLSARQLENKA 720
Mouse_iso2      KNARNDFLKEVKIMSRLKDPNIIRLLGVCVQDDPLCMITDYMENGDLNQFLSARQLENKA 683
                ************************************************************

Mouse_iso1      TQGLSGDTESDQGPTISYPMLLHVGAQIASGMRYLATLNFVHRDLATRNCLVGENFTIKI 780
Mouse_iso2      TQGLSGDTESDQGPTISYPMLLHVGAQIASGMRYLATLNFVHRDLATRNCLVGENFTIKI 743
                ************************************************************

Mouse_iso1      ADFGMSRNLYAGDYYRVQGRAVLPIRWMAWECILMGKFTTASDVWAFGVTLWEVLMLCRS 840
Mouse_iso2      ADFGMSRNLYAGDYYRVQGRAVLPIRWMAWECILMGKFTTASDVWAFGVTLWEVLMLCRS 803
                ************************************************************

Mouse_iso1      QPFGQLTDEQVIENAGEFFRDQGRQVYLSRPPACPQTLYELMLRCWSREPEQRPPFAQLH 900
Mouse_iso2      QPFGQLTDEQVIENAGEFFRDQGRQVYLSRPPACPQTLYELMLRCWSREPEQRPPFAQLH 863
                ************************************************************

Mouse_iso1      RFLADDALNTV 911
Mouse_iso2      RFLADDALNTV 874
                ***********
```

Fig. 2

DDR1-MEDIATED CELL PURIFICATION OF PANCREATIC ENDOCRINE CELLS THROUGH THEIR PROGENITORS

CROSS-REFERENCE TO RELATED APPLICATIONS

This application is a 35 U.S.C. §371 national stage application of International Patent Application PCT/EP2008/068061 (published as WO 2009/083502 A1), filed Dec. 19, 2008, which claimed priority of European Patent Application 07124132.7, filed Dec. 28, 2007; this application further claims priority under 35 U.S.C. §119 of U.S. Provisional Application 61/009,979, filed Jan. 3, 2008.

FIELD OF THE INVENTION

The invention relates to a selective cell surface marker DDR1 that permits the identification, selection and/or quantification of a unique subset of cells with pancreatic endocrine progenitor phenotype.

In one aspect compositions, cell cultures and cell populations comprising pancreatic endocrine progenitor cells and early endocrine cells are also contemplated as well as methods of producing mature endocrine cells and detecting endocrine progenitor cells and early endocrine cells. In some aspects compositions, cell cultures and cell populations comprising ductal/endocrine progenitor cells, endocrine progenitor cells, early endocrine cells and/or fully differentiated endocrine cells, are also contemplated as well as methods of producing mature endocrine cells and detecting ductal/endocrine progenitor cells, endocrine progenitor cells, and/or early endocrine cells.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jun. 28, 2010. The Sequence Listing is made up of 39 kilobytes, and the information contained in the attached "SEQUENCE LISTING" is identical to the information in the specification as originally filed. No new matter is added.

BACKGROUND OF THE INVENTION

Beta cell transplantation holds great promise to improve treatment of Type 1 diabetes but a number of obstacles need to be overcome first. Among these is the scarcity of available donor islets. Embryonic stem (ES) cell derived beta cells can in principle supply unlimited numbers of beta cells for transplantation but reliable protocols for generating fully functional beta cells are not yet developed. Formation of definitive endoderm (DE) cells from embryonic stem cells has been reported for both mouse and human ES cells in e.g. WO 2005/116073, WO 2005/063971 and US 2006/0148081. Efficient generation of pancreatic endoderm (PE) cells from e.g. DE cells is advantageous for generation of insulin-producing beta cells for the treatment of diabetes.

In attempting to cultivate adult pancreatic islet cells, the objective has long been to isolate pancreatic and pancreatic endocrine progenitor cells that are capable of differentiating into pancreatic beta cells or Islets. One important step in isolation of pancreatic endocrine progenitor cells would be to identify recognizable cell markers, specific for the pancreatic endocrine progenitor cells. In some aspects one important step in isolation of the pancreatic endocrine lineage from the acinar lineage would be to identify recognizable cell markers, specific for the pancreatic ductal/endocrine cells, pancreatic endocrine progenitor cells and pancreatic early endocrine cells. Both intracellular and extracellular markers have been investigated for this purpose. Intracellular markers, particularly those from embryonic cells that develop into mature islet cells, have been extensively studied as progenitor markers. In some aspects these intracellular markers are transcription factors detected in embryonic pancreatic cells that develop into mature islet cells. Transcription factors such as Pdx1, Ngn3, Pax6, and Isl-1, for example, have been studied. They are expressed in cells that are programmed during embryonic development to become pancreatic endocrine cells. However, these intra-cellular markers offer less practical value than extracellular markers, because analysis of expression of those markers requires either the killing of the cells or permanent modification of the cells by genetic engineering of reporter genes into the cells.

Once identified, extracellular markers would offer the advantage that the cells expressing the marker can be sorted under sterile conditions and kept alive. Epithelial cell adhesion molecules such as Ep-CAM and integrins have been investigated as pancreatic islet progenitor markers. See e.g., Cirulli et al., J. Cell Biol. 140: 1519-1534 (1998); and Cirulli et al., J. Cell Biol. 150: 1445-1460 (2000).

BRIEF DESCRIPTION OF THE DRAWINGS

FIG. 1: CLUSTAL W sequence alignment of human DDR1. Amino acid positions indicated by "–" refers to deleted amino acid positions. Amino acid positions indicated by "***" refers to positions in which the isoforms have identical amino acids. 3 isoforms are present in human. C is the longest followed by A and then B. However, the amino acid sequence on the extracellular side is identical for A, B and C. The transmembrane domain is highlighted in bold (aa 417-439). The extracellular part is amino acids 1-416.

FIG. 2: CLUSTAL W sequence alignment of mouse Ddr1. Amino acid positions indicated by "–" refers to deleted amino acid positions. Amino acid positions indicated by "*" refers to positions in which the isoforms have identical amino acids. 2 isoforms are present in mouse. 1 is the longest. However, the amino acid sequence on the extracellular side is identical for 1 and 2. The transmembrane domain is highlighted in bold (aa 415-437). The extracellular part is amino acids 1-414.

FIG. 3A shows a typical 8 μm mouse e15.5 pancreas tissue section as a schematic illustration. Cells in the mouse pancreas do not differentiate at the same time. Therefore, cells in different stages of development can be observed at a given time. At e15.5 two main domains are observed, a central and a peripheral. The central domain contains cells that have developed into early endocrine cells, endocrine progenitors, and ductal/endocrine progenitors. This central domain does not contain cells of the exocrine lineage. Cells of the acinar lineage are found in the peripheral domain. Cells in the peripheral domain are Ptf1a+ and Pdx1+, but Nk6.1–, Ddr1–. In the central domain cells are also Pdx1+, however, among the many Pdx1+ cells some cells are of the beta-cell lineage. Some of such cells of the beta-cell lineage will be positive for insulin. It is assumed that comparable cells and localisation thereof are found in the human pancreas.

FIG. 3B shows a schematic illustration of the different stages a cell passes through. In the pancreas a cell starts out being part of the multi potent pancreatic progenitor pool, i.e.

Pdx1+/Nkx6.1+/Ptf1a+. The first choice of fate made by a cell is to go either in the exocrine (Ptf1a+) or in the ductal/endocrine lineage (Pdx1+ and Nkx6.1+ or Pdx1+, Nkx6.1+, and Ddr1+ as well as Ptf1a−). Some of these cells will take the fate of the ductal lineage. When a pancreatic cell is Ddr1+ it has the potential for choosing an endocrine fate or a ductal fate and might thus later turn on Ngn3. Once the cell has turned on Ngn3 it is an endocrine progenitor cell. An Ngn3+ cell is also Pdx1+. Ngn3 expression occurs only transiently in an endocrine progenitor cell and triggers the endocrine differentiation program through particular stages where other transcription factors including NeuroD, Pax6, Arx (in alpha cells), and Pax4 (in beta cells) become activated. These transcription factors are in part responsible for activation of the hormone genes and when the early endocrine cells become positive for hormones they are almost always already negative for Ngn3 but then, e.g., Pax6+. From this time point the cells will develop into one of the fully differentiated endocrine cell types (alpha-, beta-, delta-, pp- and ghrelin-cells) depending on previous and future fate-determining inputs.

Figure 4:
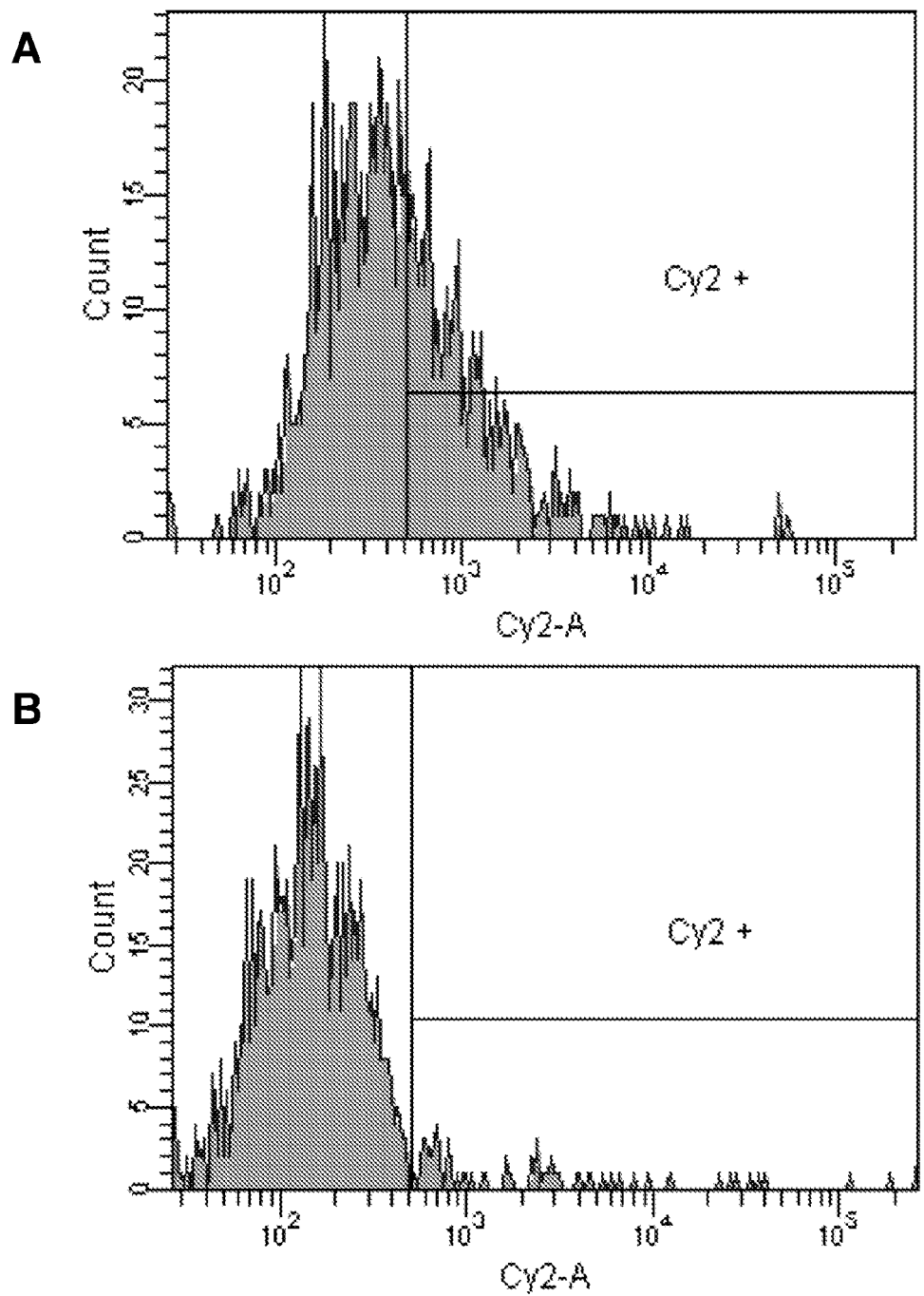

FIG. 4 shows results of sorting of mouse embryonic pancreatic cells using DDR1 via FACS. FIG. 4A shows the result using mouse anti-Ddr1 as primary antibody at 10 µg/ml. FIG. 4B shows the result using isotype (IgG2a) negative control as primary antibody at 10 µg/ml.

BRIEF SUMMARY OF THE INVENTION

The present invention discloses the use of an extracellular marker DDR1/Ddr1 for identification and selection of endocrine progenitors for pancreatic endocrine cells. In some aspects the invention relates to a method of identification of pancreatic cells comprising cells selected from the group consisting of ductal/endocrine progenitor cells, endocrine progenitor cells, and early endocrine cells, the method comprising contacting a cell population comprising pancreatic cells with a DDR1 binding reagent.

In some aspects the invention relates to a method of obtaining a culture of pancreatic cells comprising cells selected from the group consisting of ductal/endocrine progenitor cells, pancreatic endocrine progenitor cells, and early endocrine cells comprising: contacting a cell population comprising pancreatic cells with a DDR1 binding reagent and separating the cells that binds the DDR1 binding reagent in a fraction of DDR1 positive cells from cells that do not bind the DDR1 binding reagent.

In some aspects the invention relates to a method of obtaining a culture of pancreatic cells comprising cells selected from the group consisting of ductal/endocrine progenitor cells, endocrine progenitor cells, and early endocrine cells comprising: obtaining cells purified according to a method described herein and then subsequently culturing the obtained cells under conditions which facilitate their differentiation into pancreatic cells comprising cells selected from the group consisting of ductal/endocrine progenitor cells, endocrine progenitor cells, early endocrine cells, and fully differentiated endocrine cells.

In some aspects the invention relates to a method of expanding the numbers of pancreatic cells selected from the group consisting of ductal/endocrine progenitor cells, endocrine progenitor cells, and early endocrine cells comprising: obtaining cells purified according to a method described herein and then subsequently culturing the obtained cells under conditions which facilitate expansion of the cell type(s) obtained.

In some aspects the invention relates to a method of expanding the numbers of pancreatic cells selected from the group consisting of ductal/endocrine progenitor cells, endocrine progenitor cells, and early endocrine cells comprising: obtaining cells purified and expanded according to a method described herein and then subsequently culturing the obtained cells under conditions which facilitates differentiation of the cells into pancreatic cells selected from the group consisting of ductal/endocrine progenitor cells, endocrine progenitor cells, early endocrine cells, and fully differentiated endocrine cells.

In some aspects the invention relates to a method of providing pancreatic endocrine function to a mammal deficient in its production of at least one pancreatic hormone wherein cells are obtained by a method described herein, the method further comprising the steps of: implanting into the mammal the obtained cells in an amount sufficient to produce a measurable amount of at least one pancreatic hormone in the mammal.

In some aspects the invention relates to a method of quantifying DDR1 positive cells by a) contacting the cells with a DDR1 binding reagent; and b) determining the quantity of cells that exhibit DDR1 as a cell surface marker (DDR1 positive cells).

In some aspects the invention relates to a method for the optimisation of an in vitro protocol, wherein the number of DDR1 expressing cells (DDR1 positive cells) is periodically monitored.

In some aspects the invention relates to an isolated cell selected from the group consisting of ductal/endocrine progenitor cells, endocrine progenitor cells, early endocrine cells, and fully differentiated endocrine cells obtained by a method as defined herein.

In some aspects the invention relates to an isolated endocrine progenitor cell obtained by a method as defined herein.

In some aspects the invention relates to an isolated fully differentiated endocrine cell obtained by a method as defined herein.

In some aspects the invention relates to a composition comprising isolated cells selected from one or more cells from the group consisting of ductal/endocrine progenitor cells, endocrine progenitor cells, early endocrine cells, and fully differentiated endocrine cells obtained by a method as defined herein.

In some aspects the invention relates to the use of a DDR1 binding reagent to identify or select cells that express DDR1 protein as a cell surface marker.

In some aspects the invention relates to the use of DDR1 protein as a cell surface marker to obtain a culture of pancreatic endocrine cells.

One aspect of the invention relates to a method of obtaining a culture of pancreatic endocrine progenitor cells and/or early endocrine cells and/or pancreatic hormone secreting cells comprising: contacting a cell population comprising pancreatic cells with a DDR1 binding reagent and separating the cells that binds the DDR1 binding reagent in a fraction of DDR1 positive cells from cells that do not bind the DDR1 binding reagent.

Another aspect of the invention relates to a method of obtaining a culture of pancreatic endocrine cells and/or pancreatic hormone secreting cells and/or early endocrine cells and/or mature endocrine cells comprising: obtaining cells purified according to the above method and then subsequently culturing the obtained cells under conditions which facilitate their differentiation into pancreatic endocrine cells and/or pancreatic hormone secreting cells and/or early endocrine cells and/or mature endocrine cells.

In a further aspect the invention relates to a method of expanding the numbers of pancreatic endocrine progenitor cells and/or early endocrine cells and/or pancreatic hormone secreting cells comprising: obtaining cells purified according to the above method and then subsequently culturing the obtained cells under conditions which facilitate expansion of the cell type(s) obtained.

In a yet further aspect the invention relates to a method of expanding the numbers of pancreatic endocrine cells and/or pancreatic hormone secreting cells and/or early endocrine cells and/or mature endocrine cells comprising: obtaining cells purified and expanded according to the above method and then subsequently culturing the obtained cells under conditions which facilitates differentiation of the cells into pancreatic endocrine cells and/or pancreatic hormone secreting cells and/or early endocrine cells and/or mature endocrine cells.

In a further aspect, the invention relates to a method of providing pancreatic endocrine function to a mammal deficient in its production of at least one pancreatic hormone, the method comprising the steps of implanting cells obtained by any of the above-discussed methods of the invention in an amount sufficient to produce a measurable amount of said at least one pancreatic hormone in said mammal In a further aspect the invention relates method of monitoring a culture of cells comprising pancreatic cells by a) contacting the cells with a DDR1 binding reagent; and b) determining the quantity of cells that exhibit DDR1 as a cell surface marker (i.e. the DDR1 positive cells).

The DDR positive cells which are isolated in the methods of the present invention have the potential of differentiating into various pancreatic endocrine cell types. In an important aspect the DDR positive cells are differentiated further into insulin producing cells—this may be done so as to obtain insulin producing cells alone or to produce cultures of cells which also include glucagon and/or somatostatin and/or pancreatic polypeptide producing cells.

DETAILED DESCRIPTION OF THE INVENTION

DDR1 is present on pancreatic cells from the stage of differentiation from ductal/endocrine progenitor cells to early endocrine cells. Accordingly, DDR1 provides an extracellular marker of pancreatic cells at a stage of differentiation where the cells are committed to the ductal/endocrine lineage. Use of the extracellular marker DDR1 for identification, enrichment, and/or isolation of pancreatic cells provides cells which have the potential to become fully differentiated endocrine cells but have lost the potential to become exocrine cells.

Pancreatic Endocrine Cells—and their Progenitors

In the pancreas several different types of pancreatic cells may be found. The pancreatic cells include for example multipotent pancreatic progenitor cells, ductal/endocrine progenitor cells, endocrine progenitor cells, early endocrine cells, and/or fully differentiated endocrine cells. A schematic overview of these cell types can be found in FIG. 3.

"Pancreatic ductal/endocrine progenitor cells" (also termed "ductal/endocrine progenitor cells") as used herein are cells, which have lost their potential of developing into pancreatic exocrine cells, do not express Ptf1a, and are not hormone expressing, but which have the potential to differentiate into pancreatic endocrine cells or pancreatic hormone secreting cells, and which do normally also share at least part of the phenotype characteristic of these cells.

In some aspects "pancreatic endocrine progenitor cells" (also termed "pancreatic endocrine progenitors" and "endocrine progenitors") as used herein are cells, which are not hormone expressing, but which have the potential to differentiate into pancreatic endocrine cells or pancreatic hormone secreting cells, and which do normally also share at least part of the phenotype characteristic of these cells. In some aspects "pancreatic endocrine progenitor cells" (also termed "pancreatic endocrine progenitors" and "endocrine progenitors") as used herein are cells, which are Ngn3 protein expressing cells but not hormone expressing, but which have the potential to differentiate into pancreatic endocrine cells or pancreatic hormone secreting cells, and which do normally also share at least part of the phenotype characteristic of these cells.

In some aspects "pancreatic early endocrine cells" (also termed "early endocrine cells") as used herein are cells which have initiated expression of one of the pancreatic endocrine hormones (insulin, glucagon, somatostatin and pancreatic polypeptide) but do not share all the characteristics of fully mature pancreatic endocrine cells found in the Islet of Langerhans in the adult pancreas. In some aspects "pancreatic early endocrine cells" (also termed "early endocrine cells") as used herein are endocrine cells which have turned off Ngn3 but do not share all the characteristics of fully differentiated pancreatic endocrine cells found in the Islet of Langerhans in the adult pancreas, such as responsiveness to glucose, and are positive for one of the pancreatic endocrine hormones (insulin, glucagon, somatostatin, pancreatic polypeptide, and ghrelin).

In some aspects "pancreatic endocrine cell", or "pancreatic hormone expressing cell" as used interchangeably herein refers to a cell capable of expressing at least one of the following hormones: insulin, glucagon, somatostatin, and pancreatic polypeptide. In some aspects "pancreatic endocrine cell", or "pancreatic hormone expressing cell" as used interchangeably herein refers to a cell capable of expressing at least one of the following hormones: insulin, glucagon, somatostatin, pancreatic polypeptide, and ghrelin. In some aspects "pancreatic hormone secreting cell" as used herein refers to a cell capable of secreting at least one of the following hormones: insulin, glucagon, somatostatin, and pancreatic polypeptide. In some aspects "pancreatic hormone secreting cell" as used herein refers to a cell capable of secreting at least one of the following hormones: insulin, glucagon, somatostatin, pancreatic polypeptide, and ghrelin.

In some aspects "pancreatic hormone expressing cells" and "pancreatic hormone secreting cells" are considered as "pancreatic endocrine cells" ranging from the early to the fully differentiated phenotype.

"Pancreatic fully differentiated endocrine cells" (also termed "fully differentiated endocrine cells", "pancreatic mature endocrine cells" or "pancreatic adult endocrine cells") as used herein are cells which share all the characteristics of fully differentiated pancreatic endocrine cells found in the Islet of Langerhans in the adult pancreas. "beta cell lineage" as used herein refer to cells with positive gene expression for the transcription factor PDX1 and at least one of the following transcription factors: Ngn-3, Nkx2.2, Nkx6.1, NeuroD, Isl-1, Hnf-3 beta, MafA, Pax4, and Pax6. Cells expressing markers characteristic of the beta cell lineage include beta cells.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

In one aspect of the invention, the pancreatic endocrine cells are insulin producing cells. In some aspects of the invention, the pancreatic endocrine cells are insulin producing cells optionally together with cells differentiated towards glucagon, somatostatin, pancreatic polypeptide, and/or ghrelin producing cells. As used herein, "insulin producing cells" refers to cells that produce or secrete detectable amounts of insulin. In some aspects "insulin producing cells" as used herein refers to cells that produce and store or secrete detectable amounts of insulin. "Insulin producing cells" can be individual cells or collections of cells.

In some aspects of the invention, the pancreatic DDR1+ cells obtained by the method according to the invention comprise ductal/endocrine progenitor cells. In another aspect of the invention, the pancreatic DDR1+ cells obtained by the method according to the invention comprise endocrine progenitor cells. In some aspects of the invention, the pancreatic DDR1+ cells obtained by the method according to the invention comprise early endocrine cells. In some aspects of the invention, the pancreatic DDR1+ cells obtained by the method according to the invention comprise cells comprising cells selected from the group consisting of ductal/endocrine progenitor cells, endocrine progenitor cells and early endocrine cells. Such cells might be 1) non-dividing cells that are able to mature into endocrine cells. 2) dividing cells that are able to be expanded a limited number of times before maturation. 3) dividing cells that are able to undergo cell division and to be passaged from one culture vessel to another over time. A culture of propagating pancreatic cells that exhibits DDR1 as a cell surface marker refers to a culture of pancreatic progenitor cells that, in addition to detectable DDR1 cell surface expression, is capable of differentiation into mature pancreatic endocrine cells, including insulin-producing pancreatic beta cells. "Passage" of cells usually refers to a transition of a seeded culture container from a partially confluent state to a confluent state, at which point they are removed from the culture container and reseeded in a culture container at a lower density. However, cells may be passaged prior to reaching confluence. Passage typically results in expansion of the cell population as they grow to reach confluence. The expansion of the cell population depends on the initial seeding density but is typically a 1 to 10, 1 to 5, 1 to 3, or 1 to 2 fold expansion. Thus, passaging generally requires that the cells be capable of a plurality of cell divisions in culture.

Cell Population Comprising Pancreatic Cells

The term "a cell population comprising pancreatic cells" as used herein refers to a population of cells comprising one or more cell types selected from the group consisting of pancreatic endocrine progenitor cells, early pancreatic endocrine cells, pancreatic endocrine cells, pancreatic hormone secreting cells, fetal pancreatic cells, adult pancreatic cells and other non-pancreatic cells. In some aspects the term "a cell population comprising pancreatic cells" as used herein refers to a population of cells comprising one or more cell types selected from the group consisting of acinar cells, centroacinar cells, ductal cells, multi-potent pancreatic progenitor cells, ductal/endocrine progenitor cells, pancreatic endocrine progenitor cells, early pancreatic endocrine cells, pancreatic endocrine cells, pancreatic hormone secreting cells, fetal pancreatic cells, pancreatic adult endocrine cells and other non-pancreatic cells. A "population" of cells refers to a plurality of cells obtained by a particular isolation of the starting cells or culture procedure. Properties of a cell population are generally defined by a percentage of individual cells having the particular property (e.g. the percentage of cells staining positive for a particular marker) or the bulk average value of the property when measured over the entire population (e.g. the amount of mRNA in a lysate made from a cell population, or percent age of cells positive for a histochemical marker, such as Ngn3, Pax6, Insulin or Glucagon).

In one aspect of the invention, the cell population comprising pancreatic cells is obtained from a pancreas, including a fetal pancreas. In some aspects of the invention, the cell population comprising pancreatic cells is obtained from a pancreas, including a fetal pancreas or an adult pancreas. In one aspect, the pancreas is from a mammal, such as a human.

In another aspect of the invention, the cell population comprising pancreatic cells is a somatic cell population. In some aspects of the invention, the cell population comprising pancreatic cells is obtained from a somatic cell population. In a further aspect of the invention, the somatic cell population has been induced to de-differentiate in to an embryonic-like stem (ES, e.g. a pluripotent) cell. Such de-differentiated cells are also termed induced pluripotent stem cells (IPS).

In yet a further aspect, the cell population comprising pancreatic cells is embryonic stem (ES, e.g. pluripotent) cells. In yet a further aspect, the cell population comprising pancreatic cells is obtained from embryonic stem (ES, e.g. pluripotent) cells. In some aspects the cell population comprising pancreatic cells is pluripotent cells such as ES like-cells.

In yet a further aspect, the cell population comprising pancreatic cells is embryonic differentiated stem (ES or pluripotent) cells. Differentiation takes place in embryoid bodies and/or in monolayer cell cultures or a combination thereof.

In one aspect of the invention, the cell population comprising pancreatic cells is of mammalian origin. In one aspect of the invention, the cell population comprising pancreatic cells is of human origin. In some aspects of the invention, the cell population has been differentiated to the pancreatic endocrine lineage.

In one aspect of the invention, the cell population comprising pancreatic cells is obtained from one or more donated pancreases. The methods described herein are not dependent on the age of the donated pancreas. Accordingly, pancreatic material isolated from donors ranging in age from embryos to adults can be used.

Once a pancreas is harvested from a donor, it is typically processed to yield individual cells or small groups of cells for culturing using a variety of methods. One such method calls for the harvested pancreatic tissue to be cleaned and prepared for enzymatic digestion. Enzymatic processing is used to digest the connective tissue so that the parenchyma of the harvested tissue is dissociated into smaller units of pancreatic cellular material. The harvested pancreatic tissue is treated with one or more enzymes to separate pancreatic cellular material, substructures, and individual pancreatic cells from the overall structure of the harvested organ. Collagenase, DNAse, Liberase preparations (see U.S. Pat. Nos. 5,830,741 and 5,753,485) and other enzymes are contemplated for use with the methods disclosed herein.

Isolated source material can be further processed to enrich for one or more desired cell populations. In some aspects unfractionated pancreatic tissue, once dissociated for culture, can also be used directly in the culture methods of the invention without further separation. However, unfractionated pancreatic tissue, once dissociated for culture, can also be used directly in the culture methods of the invention without further separation, and will yield the intermediate cell population. In one embodiment the isolated pancreatic cellular material is purified by centrifugation through a density gradient (e.g., Nycodenz, Ficoll, or Percoll). For example the gradient method described in U.S. Pat. No. 5,739,033, can be used as a means for enriching the processed pancreatic material in islets. The mixture of cells harvested from the donor source will typically be heterogeneous and thus contain alpha cells, beta cells, delta cells, ductal cells, acinar cells, facultative progenitor cells, and other pancreatic cell types.

A typical purification procedure results in the separation of the isolated cellular material into a number of layers or interfaces. Typically, two interfaces are formed. The upper interface is islet-enriched and typically contains 10 to 100% islet cells in suspension.

The second interface is typically a mixed population of cells containing islets, acinar, and ductal cells. The bottom layer is the pellet, which is formed at the bottom of the gradient.

This layer typically contains primarily acinar cells, some entrapped islets, and some ductal cells. Ductal tree components can be collected separately for further manipulation.

The cellular constituency of the fractions selected for further manipulation will vary depending on which fraction of the gradient is selected and the final results of each isolation.

When islet cells are the desired cell type, a suitably enriched population of islet cells within an isolated fraction will contain at least 10% to 100% islet cells. Other pancreatic cell types and concentrations can also be harvested following enrichment. For example, the culture methods described herein can be used with cells isolated from the second interface, from the pellet, or from other fractions, depending on the purification gradient used.

In one aspect, intermediate pancreatic cell cultures are generated from the islet-enriched (upper) fraction. Additionally, however, the more heterogeneous second interface and the bottom layer fractions that typically contain mixed cell populations of islets, acinar, and ductal cells or ductal tree components, acinar cells, and some entrapped islet cells, respectively, can also be used in culture. While both layers contain cells capable of giving rise to the DDR1 positive population described herein, each layer may have particular advantages for use with the disclosed methods.

In one aspect of the invention, the cell population is a population of stem cells. In another aspect of the invention, the cell population is a population of stem cells differentiated to the pancreatic endocrine lineage.

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

A protocol for obtaining pancreatic cells from stem cells is exemplified by, but not limited to, the protocols described in D'Amour, K. A. et al. (2006), Nat Biotechnol 24, 1392-401; Jiang, J. et al. (2007), Stem Cells 25, 1940-53; and Kroon, E. et al. (2008), Nat Biotechnol, 2008 Feb. 20, [Epub ahead of print].

A protocol for obtaining pancreatic cells from somatic cells or somatic cells induced to de-differentiate into pluripotent cells such as ES like-cells is exemplified by, but not limited to, the protocols described in Aoi, T. et al. (2008), Science, 2008 Feb. 14, [Epub ahead of print]; D'Amour, K. A. et al. (2006), Nat Biotechnol 24, 1392-401; Jiang, J. et al. (2007), Stem Cells 25, 1940-53; Kroon, E. et al. (2008), Nat Biotechnol, 2008 Feb. 20, [Epub ahead of print]; Takahashi, K. et al. (2007), Cell 131, 861-72; Takahashi, K., and Yamanaka, S. (2006), Cell 126, 663-76; and Wernig, M. et al. (2007), Nature 448, 318-24.

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

In some aspects "differentiate" or "differentiation" as used herein refers to a process where cells progress from an immature state to a less immature state. In another aspect "differentiate" or "differentiation" as used herein refers to a process where cells progress from an undifferentiated state to a differentiated state or from an immature state to a mature state. In one aspect, for example, undifferentiated pancreatic cells are able to proliferate and express characteristics markers, like Pdx-1. In some aspects early undifferentiated embryonic pancreatic cells are able to proliferate and express characteristics markers, like Pdx1. In one aspect mature or differentiated pancreatic cells do not proliferate and secrete high levels of pancreatic endocrine hormones. In some aspects mature or differentiated pancreatic cells do not proliferate and secrete high levels of pancreatic endocrine hormones or digestive enzymes. In one aspect, e.g., mature beta cells secrete insulin at high levels. In some aspects e.g., mature beta cells secrete insulin at high levels in response to glucose. Changes in cell interaction and maturation occur as cells lose markers of undifferentiated cells or gain markers of differentiated cells. In one aspect loss or gain of a single marker can indicate that a cell has "matured or differentiated". In some aspects loss or gain of a single marker can indicate that a cell has "matured or fully differentiated". The term "differentiation factors" refers to a compound added to pancreatic cells to enhance their differentiation to mature endocrine cells also containing insulin producing beta cells. Exemplary differentiation factors include hepatocyte growth factor, keratinocyte growth factor, exendin-4, basic fibroblast growth factor, insulin-like growth factor-I, nerve growth factor, epidermal growth factor platelet-derived growth factor, and glucagon-like-peptide 1. In one aspect of the invention, differentiation of the cells comprises culturing the cells in a medium comprising one or more differentiation factors.

In one aspect markers characteristic of the pancreatic endocrine lineage are selected from the group consisting of Ngn-3, NeuroD, Islet-1, Pdx1, Nkx6.1, Nkx2.2, MafA, MafB, Arx, Brn4, Pax-4 and Pax-6, Glut2, insulin, glucagon, somatostatin, pancreatic polypeptide (PP). In some aspects markers characteristic of the pancreatic endocrine lineage are selected from the group consisting of Ngn-3, NeuroD, Islet-1, Pdx1, Nkx6.1, Nkx2.2, MafA, MafB, Arx, Brn4, Pax-4 and Pax-6, Glut2, insulin, glucagon, somatostatin, pancreatic polypeptide (PP) and ghrelin. In one embodiment, a pancreatic endocrine cell is capable of expressing at least one of the following hormones: insulin, glucagon, somatostatin, and PP. In some embodiments, a pancreatic endocrine cell is capable of expressing at least one of the following hormones: insulin, glucagon, somatostatin, PP and ghrelin. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one aspect of the present invention, the pancreatic endocrine cell is a cell expressing markers characteristic of the beta cell lineage. A cell expressing markers characteristic of the beta cell lineage expresses Pdx1 and at least one of the following transcription factors: Ngn-3, Nkx2.2, Nkx6.1, NeuroD, Isl-1, Hnf-3 beta, MafA, Pax4, and Pax6. In one aspect of the present invention, a cell expressing markers characteristic of the beta cell lineage is a beta cell. In one aspect of the invention, the pancreatic endocrine cell is a cell expressing the marker Nkx6.1. In another aspect of the invention, the pancreatic endocrine cell is a cell expressing the marker Pdx1. In a further aspect of the invention, the pancreatic endocrine cell is a cell expressing the markers Nkx6.1 and Pdx1.

"Pdx1" as used herein refers to a homeodomain transcription factor implicated in pancreas development. In one aspect "Pax-4" as used herein is a beta cell specific factor and "Pax-6" as used herein is a pancreatic islet cell (specific) transcription factor; both are implicated in islet development. In some aspects "Pax-4" as used herein is a beta cell specific transcription factor and "Pax-6" as used herein is a pancreatic islet cell specific transcription factor; both are implicated in islet development. "Hnf-3 beta" belongs to the hepatic nuclear factor family of transcription factors, which is characterized by a highly conserved DNA binding domain and two short carboxy-terminal domains. "Hnf-3 beta" is also known as "FoxA2". "NeuroD" as used herein is basic helix-loop-helix (bHLH) transcription factor implicated in neurogenesis. "Ngn-3" as used herein, is a member of the neurogenin family of basic loop-helix-loop transcription factors. "Nkx-2.2" and "Nkx-6.1" as used herein are members of the Nkx transcription factor family. "Islet-1" or "Isl-1" as used herein is a member of the LIM/homeodomain family of transcription factors, and is expressed in the developing pancreas. "MafA" as used herein is a transcription factor expressed in the pancreas, and controls the expression of genes involved in insulin biosynthesis and secretion.

Nkx6.1 and Pdx1 are co-expressed with Ptf1a in the early pancreatic multi-potent cell that can develop into all cell types found in the adult pancreas (e.g., acinar, ductal, and endocrine cells). Within this cell population cells that also transiently express Ngn3 are found. Once a cell express or has expressed Ngn3 it will be part of the endocrine lineage, giving rise to endocrine cells (one type being the insulin producing beta cell) that will later form the Islets of Langerhans. In the absence of Ngn3 no endocrine cells form during pancreas development. As development progress Nkx6.1 and Pdx1 are co-expressed in the more central domain of the pancreas which now become devoid of Ptf1a expression and the Nkx6.1 and Pdx1 positive cells can no longer give rise to acinar cells. Within this Nkx6.1 and Pdx1 positive cell population a significant number of cells transiently co-express Ngn3, marking them for the endocrine lineage like earlier in development.

DDR1

As used herein, "DDR1 protein" or "Ddr1 protein" refers to a DDR/TKT type protein kinase, Discoidin Domain Receptor family, member 1. When used herein the term may be written fully in uppercase, "DDR1", or with only the first letter in uppercase, "Ddr1", and shall mean the Discoidin Domain Receptor family, member 1 from any mammal including human and mouse. In some aspects DDR1 from mammals, such as mouse or rat, are contemplated for use in the invention. In some aspects DDR1 from a vertebrate, such as chicken, is contemplated for use in the invention. DDR1 is activated by various types of collagen, including types I through IV. Binding of collagen to DDR1 protein results in autophosphorylation and a delayed but sustained tyrosine kinase activation. DDR1 may function in cell-to-cell interaction or recognition. At least three mRNA variants, resulting in different protein isoforms of 876, 913 and 919 amino acids, have been reported in humans. In the mouse two isoforms have been reported of 874 and 911 amino acids, respectively. DDR1 protein has been shown to be overexpressed in human breast, ovarian, esophageal and pediatric brain tumors. The protein has an intracellular Receptor tyrosine kinases activity and is activated by various types of collagen. Its autophosphorylation is achieved by all collagens so far tested (type I to type VI and XI).

In some aspects the term "DDR1 protein" encompasses proteins of 70, such as 80, 85, 90, 92, 94, percent identity. In some aspects the term DDR1 protein encompasses proteins of 95, such as 96, 97, 98 or 99, percent identity. The percent identity may be determined by aligning two sequences and determining the number of aligned identical residues minus the number of different residues divided by the total number of residues in the longer sequence and multiplied by 100.

"Human DDR1 protein" as used herein is naturally occurring on chromosome c6_COX_at location 30.99-31.01 Mb or on chromosome 6 at location 6p21.3. Human DDR1 protein isoform a has GenPept accession no. NP_054699.2. Human DDR1 protein isoform b has GenPept accession no. NP_001945.3. Human DDR1 protein isoform c has GenPept accession no. NP_054700.2.

"Mouse Ddr1 protein" as used herein is naturally occurring on chromosome 17_at location 35.29-35.31 Mb or 17 C; 17 21.5 cM. Mouse DDR1 protein isoform 1 has GenPept accession no. NP_031610.2. Mouse DDR1 protein isoform 2 has GenPept accession no. NP_766550.1.

It is noted that the terms "isoform" and "isotype" are used interchangeably herein referring to different forms of the same protein formed, e.g., because of single nucleotide polymorphisms, wherein different forms of a protein may be produced from related genes or may arise from the same gene by alternative splicing. The term "DDR1 binding reagent" is used herein to refer to a compound that specifically binds to a DDR1 protein or to molecules covalently linked to a DDR1 protein, such as an antibody, an antibody fragment thereof, a synthetic, antibody derived molecule, which includes CDRs from DDR1 binding antibodies (such synthetic molecules may for example be a scFV, a multispecific antibody etc.), a lectin, and collagen types or fragments thereof.

In one aspect, the DDR1 binding reagent is an antibody that specifically binds to the DDR1 protein. In one aspect, the DDR1 binding reagent is an antibody that specifically binds to natural carbohydrates that are posttranslationally linked to the DDR1 protein; as shown in Example 1, carbohydrates are likely to appear in a number of specific sites in the DDR1 amino acid sequence. In another aspect, the DDR1 binding reagent is a lectin that specifically binds to natural carbohydrate structures linked to the DDR1 protein. In another aspect, the DDR1 binding reagent is a ligand of the DDR1 protein. In a further embodiment, the ligand is selected from the group consisting of collagens I-XI, Transthyretin, Transmembrane 4 superfamily, member 1 (TM4SF1). In another aspect, the DDR1 binding reagent is a no-toxic fluorescently marked molecule that interacts with DDR1 on the extra- or intracellular side of the plasma membrane. An "oligosaccharide linked to DDR1" is a polysaccharide molecule that is covalently linked to the DDR1 protein. In a preferred embodiment, the oligosaccharide is linked through an asparagine residue. The term "lectin" refers to protein that recognizes specific carbohydrate molecules. In a preferred embodiment the carbohydrate is all or part of an oligosaccharide linked to a DDR1 protein molecule. A "ligand" is a molecule that is specifically bound by a protein. The term also encompasses molecules that bind to a protein, for example, an antibody that specifically binds to a protein. In some instances the ligand binds to a molecule that is covalently linked to a protein, for example, a carbohydrate or an oligosaccharide.

In a preferred embodiment, the DDR1 binding reagent is an antibody that specifically binds to the DDR1 protein. The term "DDR1 binding reagent" also encompasses compounds that are specifically bound by the DDR1 protein, for example collagen and collagen fragments. The term encompasses both naturally occurring antibodies and fragments thereof, as well as chimeric antibodies composed of elements from several species and also completely synthetic antibody-like molecules such as scFVs and other synthetic molecules having the binding specificity of an antibody (as a consequence of inclusion of naturally occurring CDR sequences)

DDR1 binding reagents are used to identify or select cells that express DDR1 protein as a cell surface marker.

Cells that "exhibit DDR1 as a cell surface marker" are cells that exhibit a sufficient quantity of DDR1 on the cell surface to allow the cells to be selected or picked out from a population of cells using DDR1 specific binding reagents and methods described herein, such as FACS, immunocytochemistry, immunoadsorbtion, and panning. In some aspects the method is MACS. In a preferred embodiment a DDR1 antibody is used to select cells that "exhibit DDR1 as a cell surface marker."

In one aspect, the DDR1 binding reagent is labelled with a fluorescent dye, such as selected from PE, cy2, cy3, cy5, or Alexa488. In another aspect, the DDR1 binding reagent is labelled with a haptene such as DIG, biotin, an epitope such as FLAG, HA, or Myc.

Methods of Identification

In some aspects the invention relates to a method of identification of cells comprising cells selected from the group consisting of ductal/endocrine progenitor cells, endocrine progenitor cells, and/or early endocrine cells, the method comprising contacting a cell population comprising pancreatic cells with a DDR1 binding reagent. In a further aspect, the number and/or ratio of cells that binds the DDR1 binding reagent, i.e. DDR1 positive cells, may be determined. In some aspects the invention relates to a method of identification of pancreatic ductal/endocrine progenitor cells, the method comprising contacting a cell population comprising pancreatic cells with a DDR1 binding reagent. In some aspects the invention relates to a method of identification of endocrine progenitor cells, the method comprising contacting a cell population comprising pancreatic cells with a DDR1 binding reagent. In some aspects the invention relates to a method of identification of early endocrine cells, the method comprising contacting a cell population comprising pancreatic cells with a DDR1 binding reagent.

In some aspects the invention relates to a method of quantifying DDR1 positive cells comprising pancreatic cells by a) contacting the cells with a DDR1 binding reagent; and b) determining the quantity of cells that exhibit DDR1 as a cell surface marker (DDR1 positive cells).

Those of skill in the art will recognize that there are many methods to detect DDR1 protein. For example, antibodies that bind specifically to the DDR1 protein can be used to detect DDR1. Antibodies specific to the DDR1 protein are known to those of skill in the art and are commercially available from, for example, R&D Systems, Research Diagnostics, Inc.; Abcam; Ancell Immunology Research Products; eBioscience; the Hybridoma Bank of the Univeristy of Iowa; and Zymed Laboratories, Inc., Abnova Corporation Affinity BioReagents BioLegend, GeneTex Lifespan Biosciences, MBL International Novus Biologicals, Proteintech Group, Inc., Santa Cruz Biotechnology, Inc. Antibodies that recognize the extracellular portion of DDR1 may be used in the present invention for sorting cells. In some aspects different antibodies that recognize different epitopes on the extracellular portion of DDR1 may be used either alone or in combination. Any DDR1 binding reagents that recognize any part of DDR1 both in the extracellular domain, transmembrane domain and intracellular domain can be used for monitoring expression of DDR1. In some aspects a person skilled in the art would realise that the above description of detection of DDR1 protein would also apply to other extracellular proteins which may be contemplated for use as markers in the present invention.

Many different fluorescent molecules are available for conjugation to antibodies, for example fluorescien, cy2, cy3, cy5, PE, Alexa488, or rhodamine. Those skilled are aware that in some instances more than one extracellular marker can be detected by using different antibodies conjugated to fluorescent molecules. FACS-analysis can be done under conditions to identify more than one extracellular marker of interest.

"Antibody" or "antibodies" refer to a polypeptide comprising a framework region from an immunoglobulin gene or fragments thereof that specifically binds and recognizes an antigen. Antibodies (also known as immunoglobulins) are proteins that are found in blood or other bodily fluids of vertebrates, and are used by the immune system to identify and neutralize foreign objects, such as bacteria and viruses. Although the general structure of all antibodies is very similar, a small region at the tip of the protein is extremely variable, allowing millions of antibodies with slightly different tip structures to exist. This region is known as the hypervariable region. Each of these variants can bind to a different target, known as an antigen. This huge diversity of antibodies allows the immune system to recognize an equally wide diversity of antigens. The unique part of the antigen recognized by an antibody is called an epitope. These epitopes bind with their antibody in a highly specific interaction, called induced fit, that allows antibodies to identify and bind only their unique antigen in the midst of the millions of different molecules that make up an organism.

Methods for assessing expression of protein and nucleic acid markers in cultured or isolated cells are standard in the art and include quantitative reverse transcription polymerase chain reaction (RT-PCR), Northern blots, and in situ hybridization (see, e. g., Current Protocols in Molecular Biology (Ausubel et al., eds. 2001 supplement)) and immunoassays, such as immunohistochemical analysis of sectioned material, Western blotting, and, for markers that are accessible in intact cells, flow cytometry analysis (FACS) (see, e. g., Harlow and Lane, Using Antibodies: A Laboratory Manual, New York: Cold Spring Harbor Laboratory Press (1998)). In one aspect the nucleic acid marker may be mRNA. Conventional histochemical markers of endocrine cell differentiation may also be employed. Cells to be examfined by immunohistochemistry may be cultured on glass chamber slides for microscopic examination. Alternatively, cells grown in conventional tissue culture may be manually removed from the culture and embedded in paraffin for sectioning. Alternatively, cells grown in conventional tissue culture may be manually, enzymatically or by use of enzyme free cell dissociation buffers removed from the culture and embedded in paraffin or TissueTech for sectioning or reincubated in media before embedding. Cell differentiation markers are varied and can be detected by conventional immunohistochemistry. A generally applicable protocol follows.

In some aspects cells in chamber slides are very gently rinsed with in PBS and fixed for 45 minutes in 4% paraformaldehyde solution. Cells are then rinsed in PBS and stored at +5 until use. At the day of use cells are permeabilized through a graded series of ethanol (starting with 70% moving to 96%, then to 99%, then again 99%, then to 96%, and finally to 70%, using 5 minutes incubation with each concentration) then incubated in a blocking solution containing normal serum or TNB (from the TSA (Tyramide Signal Amplification) kit from Perkin Elmer) at room temperature. Primary antibodies are prepared at appropriate dilution and added to cells and incubated overnight (O/N) at room temperature (RT) in a moist chamber. Following incubation with primary antibody, cells were rinsed in PBS. Fluorescent secondary antibody prepared at appropriate dilution is added to the cells and incubated in the dark. With the secondary antibody DAPI dye might be included for counterstain of cell nuclei. Cells are then rinsed and excess fluid is removed and the chamber portion of the slides removed and slides are mounted with cover glass. The slides dry and are stored in the dark until inspection using a fluorescence microscope, such as a confocal microscope. In some aspects the staining process begins with removing chamber portion of the slides. Cells are very gently rinsed with in buffers and fixed in paraformaldehyde solution. Cells are then incubated in a blocking solution containing normal serum at room temperature. Cells are permeabilized with non-ionic detergent in blocking solution. Primary antibodies are prepared at appropriate dilution and added to cells and incubated. Following incubation with primary antibody, cells are rinsed in buffer. Secondary antibody prepared at appropriate dilution is added to the cells and incubated in the dark. Following incubation the cells are rinsed and nuclei were counterstained with Hoechst dye. Excess fluid is removed and the slides are mounted and covered with cover slides. Alternatively, excess fluid is removed and the slides are mounted and covered with cover glass. The slides dry and are stored in the dark.

Alternatively the cells can be prepared for immunocytochemistry using the HRP method. In brief, the cells are embedded in paraffin and slides with paraffin sections are dried at 37° C. overnight. The cells are deparaffinized and immersed in a hydrogen peroxide solution to inhibit endogenous peroxidase activity. Slides are boiled in 0.01 citrate buffer (pH 6.0) for 15 minutes to recover certain epitopes. Slides are rinsed with buffer and blocked using normal serum at room temperature in a moist chamber.

In some aspects primary antibody are added to the samples and incubated in a moist chamber. Slides are washed and incubated with biotin-secondary antibody. Slides were again rinsed with buffer and incubated with Avidin-HRP. Slides are again rinsed and incubated with TSA reagent to visualize primary antibody. In some aspects TSA is an abbreviation for tyramide signal amplification. Slides are mounted for viewing.

Alternatively, the cells can be prepared for immunocytochemistry using the HRP (horse-radish peroxidise) method. As secondary antibody a biotin coupled one is used. Slides were then rinsed with PBS and incubated with Avidin-HRP. Slides are again rinsed and incubated with TSA reagent to visualize primary antibody. Slides are mounted for visual inspection using a fluorescence microscope, such as a confocal microscope. In some aspects the development may be carried out using a chromogene reagent, such as AEC. In some aspects the development may be visualised by conventional light microscopy.

For the identification of proteins in tissue sections the tissue is fixed in 4% PFA (paraformaldehyde) O/N, then cryo-protected in 30% sucrose O/N and imbedded in TissueTech. Sections are then cut on a cryostate, rinsed in PBS (phosphate buffered saline) and microwaved in 0.01 M citrate buffer (pH 6.0) for 15 minutes to recover epitopes. Such sections can then be stained using either method above, but omitting the graded ethanol treatment. A hydrogen peroxide solution was used to inhibit endogenous peroxidase activity in the case of using the HRP based assay. In some aspects sections are then cut on a microtome, such as when using paraffin sections.

Analytical FACS sorting is carried out on live cells or cells that have been fixed for 45 minutes in Lillys fixative. To remove supernatant cells are pelleted by 1300 rpm in 5 minutes at RT in 10 ml v-tubes. Following this cells are washed in PBS with 0.1% BSA. For fixed cells: Cells are blocked by adding serum to reach 10% serum (final concentration) from the animal where the secondary antibody is raised, block for 1 h. Cells are then pelleted and supernatant removed. Primary antibody solution is added and incubated O/N at RT. The next day cells are washed 2×5 minutes in 10 ml v-tubes. Secondary antibody is added and incubated for 1 hour at RT. Cells are washed 2×5 min in PBS with 0.1% BSA in 10 ml v-tubes. Finally, cells are assayed by FACS. Live cells: Primary antibody solution is added and incubated 1 hour at 4° C. Cells are washed 2×5 minutes in 10 ml v-tubes. Secondary antibody is added and incubated for 30 minutes at 4 degrees. Cells are washed 2×5 min in PBS with 0.1% BSA in 10 ml v-tubes. Finally, cells are fixed and assayed by FACS.

Identification of ductal/endocrine progenitor cells, endocrine progenitor cells, and/or early endocrine cells may be achieved by contacting the cell population with a DDR1 binding reagent and evaluating the staining. In a specific embodiment, identification of endocrine progenitor cells may be achieved by contacting the cell population with a DDR1 binding reagent and evaluating the staining. In another specific embodiment, identification of endocrine progenitor cells may be achieved by contacting the cell population with a DDR1 binding reagent and evaluating the staining. This analysis may be carried out using a method such as fluorescence activated cell sorting (FACS), immunohistochemistry (IHC), western blot, PCR, or ELISA.

In some aspects the invention relates to an isolated cell selected from the group of ductal/endocrine progenitor cells, endocrine progenitor cells, and early endocrine cells obtained by a method as defined herein. In some aspects the invention relates to an isolated endocrine progenitor cell obtained by a method as defined herein. In a further aspect, the isolated cell is an endocrine progenitor cell. In some aspects the invention relates to an isolated endocrine progenitor cell obtained by a method as defined herein.

In some aspects the invention relates to the use of a DDR1 binding reagent to identify or select cells that express DDR1 protein as a cell surface marker. In some aspects the invention relates to the use of DDR1 protein as a cell surface marker to obtain a culture of pancreatic endocrine cells. In a further aspect, one or more further cell surface markers are used simultaneously or sequentially to obtain a culture of pancreatic endocrine cells. In yet a further aspect, a further cell surface marker is selected from the group consisting of prominin 1 (also known as CD133), and CD49f.

Methods of Separating

In some aspects the invention relates to a method of obtaining a culture of cells comprising cells selected from the group consisting of ductal/endocrine progenitor cells, endocrine progenitor cells, and/or early endocrine cells, the method comprising: contacting a cell population comprising pancreatic cells with a DDR1 binding reagent and separating the cells that binds the DDR1 binding reagent in a fraction of DDR1 positive cells from cells that do not bind the DDR1 binding reagent. In some aspects the invention relates to a method of obtaining a culture comprising the method comprising: contacting a cell population comprising pancreatic cells with a DDR1 binding reagent and separating the cells that binds the DDR1 binding reagent in a fraction of DDR1 positive cells from cells that do not bind the DDR1 binding reagent. In some aspects the invention relates to a method of obtaining a culture comprising endocrine progenitor cells, the method comprising: contacting a cell population comprising pancreatic cells with a DDR1 binding reagent and separating the cells that binds the DDR1 binding reagent in a fraction of DDR1 positive cells from cells that do not bind the DDR1 binding reagent.

In some aspects, the step of separating is done by fluorescence activated cell sorting (FACS). In another aspect, the step of separating is done by panning. In some aspects, the step of separating is done by magnetic activated cell sorting (MACS).

Fluorescently labelled molecules that bind specifically to DDR1, most commonly antibodies, are used to select DDR1 positive cells in conjunction with a Fluorescence Activated Cell Sorter (FACS). Briefly, in one aspect, a cell population comprising pancreatic cells are incubated with fluorescently labelled antibody and after the antibody binding, the cells are analyzed by FACS. The cell sorter passes single cells suspended in liquid through a fluorimeter. The amount of fluorescence is measured and cells with fluorescence levels detectably higher than control, unlabeled, cells are selected as positive cells.

FACS can also be used to physically separate cell populations based on measurement of fluorescence. The flowing cells are deflected by electromagnetic fields whose strength and direction are varied according to the measured intensity of the fluorescence signal. Labelled DDR1 positive cells can be deflected into a separate container and thus, separated from unlabeled DDR1 negative cells.

In the aspect, wherein the cell population comprising pancreatic cells are isolated from pancreas, the cells are first cultured for one or more passages and then labelled with a DDR1 specific antibody. The cells are then scanned using FACS to separate DDR1 positive from DDR1 negative cells. While this example has discussed FACS analysis with labelled antibodies, other molecules that specifically bind to DDR1, e.g., lectins and collagens and other DDR1 binding partners, such as listed above, can also be used to practice the invention.

In another aspect, the method of separating DDR1 positive cells from DDR1 negative cells is by affinity adsorbing DDR1 positive cells onto a solid support.

DDR1 positive cells can also be separated from DDR1 negative cells by using DDR1 specific binding molecules attached to a solid support. Those of skill in the art will recognize that DDR1 specific antibodies can be bound to a solid support through an antibody binding molecule, such as protein G or protein A or alternatively, can be conjugated to a solid support directly. Solid supports with attached DDR1 antibodies are commercially available, e.g., StemSep and EasySep™, magnetic beads from both from Stem Cell Technologies. The step of separating may be carried out using magnetic activated cell sorting (MACS).

DDR1 positive cells can also be separated from DDR1 negative cells through the technique of panning. Panning is done by coating a solid surface with a DDR1 binding reagent and incubating pancreatic cells on the surface for a suitable time under suitable conditions. A flat surface, e. g., a culture dish, is coated with a DDR1 binding reagent.

Pancreatic cells are added to the surface and allowed to bind to the DDR1 binding reagent.

The culture dishes are then washed, removing the DDR1 negative cells from the dish. In a preferred embodiment, a DDR1 specific antibody is used to coat a culture dish and "pan" for DDR1 positive cells in a population of pancreatic cells.

In one aspect, the cells may be purified before or after selection by DDR1 by separating cells into Ptprn/IA2-positive and Ptprn-negative cells. In another aspect, the cells may be separated into Abcc8/Sur1-positive and Abcc8/Sur1-negative cells. In another aspect the cells may be separated into (Glut2 or Glut1)-positive and (Glut2 or Glut1)-negative cells. In another aspect, the cells may be separated into Slc30a8/ZnT-8-positive and Slc30a8/ZnT-8-negative cells.

So, the invention includes embodiments where wherein the cell population comprising pancreatic cells is a Ptprn-positive fraction and/or a Abcc8-positive fraction and/or a Glut-2/1-positive fraction and/or a Slc30a8-positive fraction. Also, the culture of pancreatic endocrine cells obtained by the method according to any of the above claims may be further separated in a Ptprn-positive/negative fraction and/or an Abcb9-positive/negative fraction and/or a Glut-2/1-positive/negative fraction and/or a Slc30a8-positive/negative fraction.

A person skilled in the art will realise that all details in the section above relating to methods of separating, although explicitly stated for DDR1, may also be applied to other extracellular proteins. Such extracellular protein include proteins selected from the group consisting of DDR1, prominin 1 (also known as CD133), and CD49f.

During differentiation of embryonic stem (ES) cells into beta cells it is expected that other cells types, such as, e.g., neural cells, and non-pancreatic endoderm will also be produced. ES cells can be differentiated to endodermal cells by activin A and then to pancreatic cells. Once the pancreatic fate has been acquired the wanted cells can be isolated. DDR1, optionally in combination with one or more additional markers, can then be used as a marker to isolate the wanted subset of cells. A DDR1 binding reagent also binds to other endodermal cells than pancreatic cells. A DDR1 binding reagent will bind the endocrine cells of the esophagus to the anterior stomach and the small intestine in addition to pancreatic cells. A DDR1 binding reagent will not bind to differentiated neural cells.

Various strategies for identification, enrichment, and/or selection are available, such as the following example: ES cells that have been induced to differentiate into definitive endoderm including pancreatic endoderm can be subjected to the use of DDR1 as a marker to isolate DDR1+ cells. This step will allow direct isolation of the ES-derived pool of cells that can be designated ductal/endocrine progenitor cells, pancreatic endocrine progenitor cells, and/or pancreatic early endocrine progenitor cells. Upon further in vitro mediated differentiation of such cells the subsequent use markers of, e.g., Ptprn/IA2-, Abcc8/Sur1-, or Slc30a8/ZnT-8-positive cells as markers can be used to isolate early and fully differentiated endocrine cells.

In some aspects of the invention, using DDR1 as a marker, optionally in combination with one or more additional markers, will provide a cell population comprising ductal/endocrine progenitor cells, endocrine progenitor cells, and/or early endocrine cells with a low ratio of other cell types, such as less than 20%, less than 15%, less than 10%, less than 5%, less than 2%, or no other cell types, such as endodermal cells other than pancreatic cells.

In one embodiment compositions comprising pancreatic endocrine cells substantially free of other cell types may be produced. In some embodiments compositions comprising pancreatic ductal/endocrine progenitor cells, pancreatic endocrine progenitor cells, early endocrine cells, and fully differentiated endocrine cells substantially free of other cell types may be produced. In some embodiments compositions comprising pancreatic endocrine progenitor cells substantially free of other cell types may be produced. In some embodiments compositions comprising pancreatic endocrine progenitor cells substantially free of other cell types may be produced. In some aspects of the invention, the expression "substantially free of" is for cell cultures or cell populations to be understood as a cell culture or cell population comprising less than 20% other cell types than pancreatic ductal/endocrine progenitor cells, endocrine progenitor cells, early endocrine cells and fully differentiated endocrine cells in relation to the total number of cells. In some aspects of the invention, the expression "substantially free of" is for cell cultures or cell populations to be understood as a cell culture or cell population comprising less than 20% other cell types than pancreatic ductal/endocrine progenitor cells in relation to the total number of cells. In some aspects of the invention, the expression "substantially free of" is for cell cultures or cell populations to be understood as a cell culture or cell population comprising less than 20% other cell types than pancreatic endocrine progenitor cells in relation to the total number of cells. In some aspects of the invention, the expression "substantially free of" is for cell cultures or cell populations to be understood as a cell culture or cell population comprising less than 20% other cell types than pancreatic early endocrine cells in relation to the total number of cells.

In some embodiments the invention relates to a method wherein the resulting cell population consists of at least 30%, such as at least 40%, at least 50%, at least 60%, at least 70%, at least 80%, at least 90%, or at least 95% cells selected from the group consisting of ductal/endocrine progenitor cells, endocrine progenitor cells, early endocrine cells and/or fully differentiated endocrine cells. In some embodiments the invention relates to a method wherein the resulting cell population consists of at least 30%, such as at least 40%, at least 50%, at least 60%, at least 70%, at least 80%, at least 90%, or at least 95% ductal/endocrine progenitor cells. In some embodiments the invention relates to a method wherein the resulting cell population consists of at least 30%, such as at least 40%, at least 50%, at least 60%, at least 70%, at least 80%, at least 90%, or at least 95% endocrine progenitor cells. In some embodiments the invention relates to a method wherein the resulting cell population consists of at least 30%, such as at least 40%, at least 50%, at least 60%, at least 70%, at least 80%, at least 90%, or at least 95% early endocrine cells.

In some embodiments the invention relates to a method wherein the starting cell population is of endodermal origin and the resulting cell population consists of at least 30%, such as at least 40%, at least 50%, at least 60%, at least 70%, at least 80%, at least 90%, or at least 95% cells selected from the group consisting of ductal/endocrine progenitor cells, endocrine progenitor cells, early endocrine cells and/or fully differentiated endocrine cells. In some embodiments the invention relates to a method wherein the starting cell population is of endodermal origin and the resulting cell population consists of at least 30%, such as at least 40%, at least 50%, at least 60%, at least 70%, at least 80%, at least 90%, or at least 95% cells selected from the group consisting of ductal/endocrine progenitor cells. In some embodiments the invention relates to a method wherein the starting cell population is of endodermal origin and the resulting cell population consists of at least 30%, such as at least 40%, at least 50%, at least 60%, at least 70%, at least 80%, at least 90%, or at least 95% endocrine progenitor cells. In some embodiments the invention relates to a method wherein the starting cell population is of endodermal origin and the resulting cell population consists of at least 30%, such as at least 40%, at least 50%, at least 60%, at least 70%, at least 80%, at least 90%, or at least 95% early endocrine cells.

In some embodiments the invention relates to a method wherein the starting cell population comprises cells of endodermal and/or neural origin and the resulting cell population consists of at least 30%, such as at least 40%, at least 50%, at least 60%, at least 70%, at least 80%, at least 90%, or at least 95% cells selected from the group consisting of ductal/endocrine progenitor cells, endocrine progenitor cells, early endocrine cells and/or fully differentiated endocrine cells. In some embodiments the invention relates to a method wherein the starting cell population comprises cells of endodermal and/or neural origin and the resulting cell population consists of at least 30%, such as at least 40%, at least 50%, at least 60%, at least 70%, at least 80%, at least 90%, or at least 95% cells selected from the group consisting of ductal/endocrine progenitor cells. In some embodiments the invention relates to a method wherein the starting cell population comprises cells of endodermal and/or neural origin and the resulting cell population consists of at least 30%, such as at least 40%, at least 50%, at least 60%, at least 70%, at least 80%, at least 90%, or at least 95% cells selected from the group consisting of endocrine progenitor cells. In some embodiments the invention relates to a method wherein the starting cell population comprises cells of endodermal and/or neural origin and the resulting cell population consists of at least 30%, such as at least 40%, at least 50%, at least 60%, at least 70%, at least 80%, at least 90%, or at least 95% cells selected from the group consisting of early endocrine cells. In some embodiments the invention relates to a method wherein the DDR1 binding reagent simultaneously or sequentially is used in combination with one or more additional binding reagents when the starting cell population comprises cells of endodermal and neural origin wherein the starting cell population comprises cells of endodermal and/or neural origin. In some embodiments the invention the additional binding reagent is selected from the group consisting of prominin 1 (also known as CD133), and CD49f binding reagent.

In some aspects the invention relates to an isolated cell selected from the group consisting of ductal/endocrine progenitor cells, endocrine progenitor cells, early endocrine cells and fully differentiated endocrine cells obtained by any of the methods defined herein. In some aspects the invention relates to an isolated ductal/endocrine progenitor cell obtained by a method as defined in any of the methods defined herein. In some aspects the invention relates to an isolated endocrine progenitor cell obtained by a method as defined in any of the methods defined herein. In some aspects the invention relates to an isolated early endocrine cell obtained by a method as defined in any of the methods defined herein. In some aspects the invention relates to an isolated fully differentiated endocrine cell obtained by a method as defined in any of the methods defined herein.

In some aspects the invention relates to a composition comprising isolated cells selected from one or more cells from the group consisting of ductal/endocrine progenitor cells, endocrine progenitor cells, early endocrine cells and fully differentiated endocrine cells obtained by a method as defined in any of the methods defined herein. In some aspects the invention relates to a composition comprising isolated endocrine progenitor cells obtained by a method as defined in any of the methods defined herein. In some aspects the invention relates to a composition comprising isolated fully differentiated endocrine cells obtained by a method as defined in any of the methods defined herein.

Cell Differentiation Markers

In some aspects the invention relates to a method of obtaining a culture of cells comprising cells selected from the group consisting of ductal/endocrine progenitor cells, endocrine progenitor cells, and/or early endocrine cells, the method comprising: obtaining cells purified according to the methods described herein and then subsequently culturing the obtained cells under conditions which facilitate differentiation of the pancreatic cells into cells selected from the group consisting of ductal/endocrine progenitor cells, endocrine progenitor cells, early endocrine cells and/or fully differentiated endocrine cells. In some aspects the invention relates to a method of obtaining a culture comprising ductal/endocrine progenitor cells the method comprising: obtaining cells purified according to the method described above and then subsequently culturing the obtained cells under conditions which facilitate differentiation of the pancreatic cells into cells selected from the group consisting of ductal/endocrine progenitor cells, endocrine progenitor cells, early endocrine cells and/or fully differentiated endocrine cells. In some aspects the invention relates to a method of obtaining a culture comprising endocrine progenitor cells, the method comprising: obtaining cells purified according to the methods described herein and then subsequently culturing the obtained cells under conditions which facilitate differentiation of the pancreatic cells into cells selected from the group consisting of endocrine progenitor cells, early endocrine cells and/or fully differentiated endocrine cells.

There are a number of cellular markers that can be used to identify populations of pancreatic cells. Donor cells isolated and cultured begin to display various phenotypic and genotypic indicia of differentiated pancreatic cells. Examples of the phenotypic and genotypic indicia include various molecular markers present in the facultative progenitor cell population that are modulated (e.g., either up or down regulated). These molecular markers include CK-19 or the Pdx1/Nkx6.1/Ptf1a triple positive cell, which is hypothesized to be a marker of the pancreatic facultative stem cell.

Typically, mammalian stem cells proceed through a number of developmental stages as they mature to their ultimate developmental endpoint. Developmental stages often can be determined by identifying markers present or absent in developing cells. Because human endocrine cells develop in a similar manner, various markers can be used to identify cells as they transition from a stem cell-like phenotype to pseudo-islet phenotype.

The expression of markers in cells induced to proliferate or differentiate by the methods of the present invention bears some similarity to the sequence of marker expression in normal human pancreas development. Very early in development, the primordial epithelial cells express Pdx-1, an early cellular marker that is a homeodomain nuclear factor. As the cells develop, they begin to bud out and form a duct. These cells express cytokeratin 19, a marker for epithelial ductal cells, and temporally express Pdx-1 leading developmentally to endocrine cells. As these cells continue to develop towards endocrine cells, they gain the ability to express insulin, somatostatin, glucagon or pancreatic polypeptide. The final differentiated cells are only able to express one and become the alpha cells (glucagon), beta cells (insulin), delta cells (somatostatin) and PP-cells. The DDR1 positive cell population used herein is believed to be at a less than fully differentiated stage of development, retaining the potential to differentiate into mature endocrine cells and the ability to proliferate. Whether the cells are indeed examples of a precursor in the development pathway or simply a result of in vitro manipulation, the DDR1 positive cells are believed to be able to proliferate as well as to eventually express endocrine hormones or to mature from pancreatic early endocrine cells to a more mature endocrine cell type and, therefore, have the potential for being used to correct a deficiency in any type of islet cell.

It is believed that the DDR1 positive cell population used herein can be divided into the main categories of ductal/endocrine progenitor cells, endocrine progenitor cells, and/or early endocrine cells.

Figure 3:
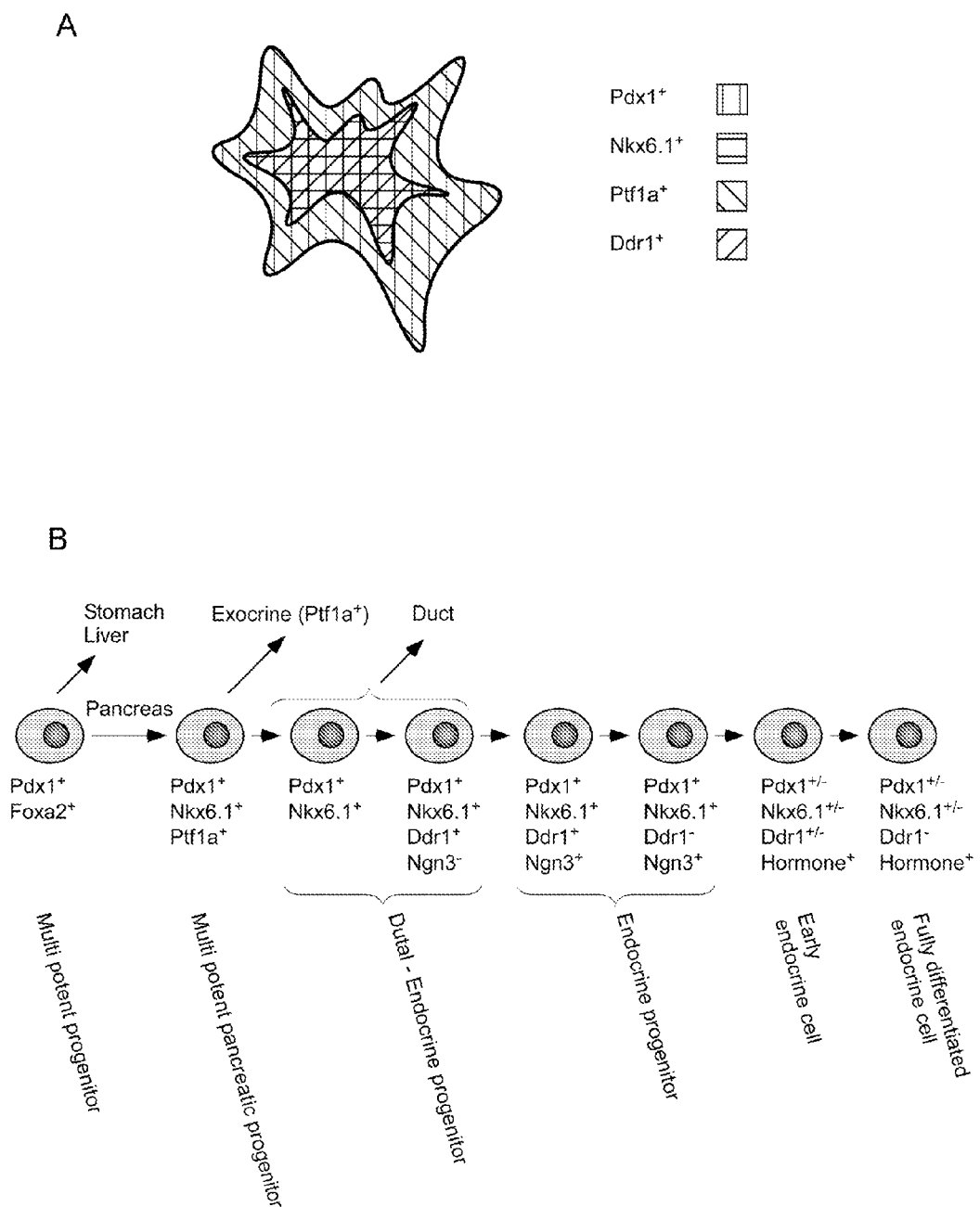
FIG. 3 shows a schematic illustration of the development pathway of pancreatic cells.

The extracellular expression of DDR1 may vary in different domains of the pancreas and changes during the stages of development of pancreatic endocrine cells, see, e.g., schematic overview in FIG. 3.

DDR1 is expressed in some cells of the pancreatic endoderm. DDR1 is not expressed in the multi-potent Pdx1+/Nkx6.1+/Ptf1a+ pancreatic progenitor cell. DDR1 is not expressed in the exocrine lineage. DDR1 appears to be expressed in the ductal/endocrine progenitor cell. Thus, DDR1 can be used to identify, enrich, and/or isolate ductal/endocrine progenitor cells. DDR1 is expressed in the endocrine progenitor cell. Thus, DDR1 can be used to identify, enrich, and/or isolate endocrine progenitor cells. DDR1 may be expressed at high, medium or low levels in the endocrine progenitor cell. Thus, DDR1 can be used to identify, enrich, and/or isolate endocrine progenitor cells. DDR1 may be expressed at high, medium or low levels in the early endocrine cell. Thus, DDR1 can also be used to identify, enrich, and/or isolate early endocrine cells. Accordingly, DDR1 may be used to identify, enrich, and/or isolate pancreatic cells selected from the group consisting of ductal/endocrine progenitor cells, endocrine progenitor cells, and/or early endocrine cells. Specifically, while many proteins, such as Ptprn/IA2, Abcc8/Sur1, and Slc30a8/ZnT-8, can be used to identify, enrich, and/or isolate early endocrine cells and/or fully differentiated endocrine cells, only DDR1 may be used to identify, enrich, and/or isolate endocrine progenitor cells.

The DDR1 positive cells are believed to be examples of a precursor in the development pathway which are able to differentiate into cells that eventually express endocrine hormones or to mature from pancreatic early endocrine cells to a more mature endocrine cell type and, therefore, have the potential to be used to correct a deficiency in any type of Islet cell.

Furthermore, the DDR1 positive cell population is believed to be at a less than fully differentiated stage of development, retaining the potential to differentiate into fully differentiated endocrine cells and the ability to proliferate. The DDR1 positive cells are believed to be examples of a precursor in the development pathway which are able to proliferate as well as to differentiate into cells that eventually express endocrine hormones or to mature from pancreatic early endocrine cells to a more mature endocrine cell type and, therefore, have the potential for being used to correct a deficiency in any type of Islet cell.

Markers of interest are molecules that are expressed in temporal- and tissue-specific patterns in the pancreas (see Hollingsworth, Ann NY Acad Sci 880: 38-49 (1999)). These molecular markers are divided into three general categories: transcription factors, notch pathway markers, and intermediate filament markers. Examples of transcription factor markers include Pdx-1, NeuroD, Nkx-6.1, Isl-1, Pax-6, Pax-4, Ngn-3, and HES-1.

Examples of notch pathway markers include Notch1, Notch2, Notch3, Notch4, Jagged1, Jagged2, Dll1, and RBPjk. Examples of intermediate filament markers include CK19 and nestin. Examples of markers of precursors of pancreatic beta cells include Pdx-1, Pax-4, Ngn-3, and Hb9. In some aspects examples of markers of mature pancreatic flcells include insulin, somatostatin, glp-9, and glucagon. In some aspects examples of markers of mature pancreatic beta cells include insulin, Ptprn/IA2, Abcc8/Sur1, and Slc30a8/ZnT-8.

Insulin mRNA Expression

One marker that may be used to characterize pancreatic cell identity, differentiation, or maturity is the level of insulin mRNA. For example, the intermediate cell population of the present invention show expression of insulin mRNA within a defined range. Method for quantitating insulin mRNA include Northern blots, nuclease protection, and primer extension.

In one embodiment, RNA is extracted from a population of cultured cells, and the amount of proinsulin message is measured by quantitative reverse transcription PCR. Following reverse transcription, insulin cDNA is specifically and quantitatively amplified from the sample using primers hybridizing to the insulin cDNA sequence, and amplification conditions under which the amount of amplified product is related to the amount of mRNA present in the sample (see, e.g., Zhou et al., J Biol Chem 272: 25648-51 (1997)). Kinetic quantification procedures are preferred due to the accuracy with which starting mRNA levels can be determined.

Frequently, the amount of insulin mRNA is normalized to a constitutively expressed mRNA such as actin, which is specifically amplified from the same RNA sample using actin-specific primers. Thus, the level of expression of insulin mRNA may be reported as the ratio of insulin mRNA amplification products to actin mRNA amplification products, or simply the insulin:actin mRNA ratio. The expression of mRNAs encoding other pancreatic hormones (e.g., somatostatin or glucagon) may be quantitated by the same method. Insulin and actin mRNA levels can also be determined by in situ hybridization and then used to determine insulin: actin mRNA ratios. In situ hybridization methods are known to those of skill in the art.

Methods of Expansion

In some aspects the invention relates to a method of expanding the numbers of cells comprising cells selected from the group consisting of ductal/endocrine progenitor cells, endocrine progenitor cells, and/or early endocrine cells, the method comprising: obtaining cells purified according to the method described above and then subsequently culturing the obtained cells under conditions which facilitate expansion of the cell type(s) obtained. In some aspects the invention relates to a method of expanding the numbers of the method comprising: obtaining cells purified according to the method described above and then subsequently culturing the obtained cells under conditions which facilitate expansion of the endocrine progenitor cells. In some aspects the invention relates to a method of expanding the numbers of endocrine progenitor cells, the method comprising: obtaining cells purified according to the method described above and then subsequently culturing the obtained cells under conditions which facilitate expansion of endocrine progenitor cells.

In some aspects the invention relates to a method of expanding the numbers of cells comprising cells selected from the group consisting of ductal/endocrine progenitor cells, endocrine progenitor cells, and/or early endocrine cells, the method comprising: obtaining cells purified and expanded according to the method described above and then subsequently culturing the obtained cells under conditions which facilitates differentiation of the pancreatic cells into cells selected from the group consisting of ductal/endocrine progenitor cells, endocrine progenitor cells, early endocrine cells and/or fully differentiated endocrine cells. In another further aspect the invention relates to a method of expanding the numbers of ductal/endocrine progenitor cells the method comprising: obtaining cells purified and expanded according to the method described above and then subsequently culturing the obtained cells under conditions which facilitates differentiation of the endocrine progenitor cells. In yet another further aspect the invention relates to a method of expanding the numbers of endocrine progenitor cells, the method comprising: obtaining cells purified and expanded according to the method described above and then subsequently culturing the obtained cells under conditions which facilitates differentiation of the endocrine progenitor cells. In yet another further aspect the invention relates to a method of expanding the numbers of early endocrine cells, the method comprising: obtaining cells purified and expanded according to the method described above and then subsequently culturing the obtained cells under conditions which facilitates differentiation of the endocrine progenitor cells.

A protocol for expansion of pancreatic cells derived from fetal/adult tissue and stem cells is exemplified by, but not limited to, the protocols described in Heimberg, H. et al. (2000), Diabetes 49, 571-9; Heremans, Y. et al. (2002), J Cell Biol 159, 303-12; Miralles, F. et al. (1998), Development 125, 1017-24; and Miralles, F. et al. (1999), Dev Dyn 214, 116-26.

Functional Assays

One of the important functions of a beta cell is to adjust its insulin secretion according to the glucose level. Typically, a static glucose stimulation (SGS) assay can be performed on the proliferating adherent pancreatic cells to identify whether they are able to secrete insulin in response to different glucose levels. Cells are generally cultured on an appropriate substrate until nearly confluent. Three days prior to the SGS test, the culture medium is replaced by a medium of similar character but lacking insulin and containing only 1 g/L of glucose. The medium is changed each day for three days and the SGS test is performed on day four.

Before the test, the culture medium may be collected for glucose and insulin analysis. To prepare cells for the test, cells are washed twice with Dulbecco's phosphate-buffered saline (DPBS)+0.5% BSA, incubating for 5 minutes with each wash, and then once with DPBS alone, also incubating for 5 minutes. After washing, the cells are incubated with 10 ml (in a 100 mm dish) or 5 ml (in a 60 mm dish) of Krebs-Ringers SGS solution with 60 mg/dl glucose (KRB-60) for 30 minutes in a 37° C. incubator. This incubation is then repeated.

To perform the SGS assays, cells are incubated in 3 ml (100 mm dish) or 4 ml (T75 flask) or 2 ml (60 mm dish) KRB-60, at 37° C. for 20 minutes. The medium is aspirated and spun, and is collected for insulin assay as LG-1 (low glucose stimulated step). KRB-450+theo (KRB with 450 mg/dl glucose and 10 mM theophylline) is then added with the same volume as above, and cells are cultured under the same condition as above. The supernatant is collected for insulin assay as HG (high glucose stimulated). The cells are then incubated again with KRB-60 and the medium collected as LG-2, and another time as LG-3. The media are collected for insulin analysis, and stored at −20° C. until insulin content is determined by radioimmunoassay (RIA) or other suitable assay.

The results of the SGS test are often expressed as a stimulation index, defined as the HG insulin value divided by the LG-1 insulin value. Generally, a stimulation index of about 2 or greater is considered to be a positive result in the SGS assay, although other values (e.g., 1.5, 2.5, 3.0, 3.5, etc.) may be used to define particular cell populations.

Treatment Methods

In some aspects the invention relates to a method of providing pancreatic endocrine function to a mammal deficient in its production of at least one pancreatic hormone wherein cells are obtained by any of the methods described above, the method further comprising the steps of: implanting into the mammal the obtained cells in an amount sufficient to produce a measurable amount of at least one pancreatic hormone in the mammal.

In some aspects the amount of pancreatic hormone is determined no earlier than the day after the transplantation. In some aspects and when carrying out transplantation using differentiated pancreatic cells beta cell function, such as measurement of pancreatic hormone and blood glucose levels, should be carried out right after transplantation, such as before 12 hours, before 24 hours, or before 36 hours after the transplantation.

In some aspects the amount of pancreatic hormone is determined after in vivo maturation, such as at least 1, 2, 3 or 4 weeks after transplantation. In some aspects and in the case of carrying out transplantation using pancreatic cells comprising immature pancreatic cells, measurement of beta cell function, such as measurement of pancreatic hormone and blood glucose levels, should be carried out at least 2 weeks, such as at least 4 weeks, at least 6 weeks, or at least 8 weeks after the transplantation. Those of skill in the art will recognize that DDR1 selected cells or further cultured and differentiated cells provide a renewable resource for implantation and restoration of pancreatic function in a mammal.

DDR1 positive pancreatic cells are first differentiated before implantation into the mammal. Alternatively, DDR1 selected cells are implanted in the progenitor state and allowed to differentiate in the body. If desired by the user, DDR1 cells can be encapsulated before implantation.

Differentiation of DDR1 positive pancreatic cells before implantation into the mammal may be to the stages of differentiation selected from the group consisting of fully differentiated endocrine cells, including glucose responsive insulin producing beta cells, i.e. equivalent to beta cells of the isolated Islet of Langerhans. An example of implantation isolated Islet of Langerhans using the so-called Edmonton protocol can be found in Shapiro A M (2000), N Engl J Med.; 343(4):230-8.

Cells selected by DDR1 may be implanted in the progenitor state, i.e. immature cells, such as a cell population comprising cells selected from the group consisting of pancreatic ductal/endocrine progenitor cells, pancreatic progenitor cells, and/or early endocrine cells, and allowed to differentiate in the body. In one embodiment, cells selected by DDR1 may be implanted in the progenitor state of pancreatic progenitor cells. In some embodiments, cells selected by DDR1 may be implanted in the progenitor state of pancreatic progenitor cells. Accordingly, the DDR1-positive cells may be used directly for transplantation. In this situation, the in vivo environment is anticipated to cause the DDR1+ cells to differentiate into therapeutic beta cells. An example of the use of immature pancreatic cells for transplantation is described in Kroon E et al. (2008), Nat Biotechnol, 2008 Feb. 20 [Epub ahead of print].

Encapsulation of the DDR1 positive cells results in the formation of cellular aggregates in the capsules. Encapsulation can allow the pancreatic cells to be transplanted into a type 1 diabetic host, while minimizing the immune response of the host animal. The porosity of the encapsulation membrane can be selected to allow secretion of biomaterials, like insulin, from the capsule, while limiting access of the host's immune system to the foreign cells.

Encapsulation methods are known in the art and are disclosed in the following references: van Schelfgaarde & de Vos, J. Mol. Med. 77: 199-205 (1999), Uludag et al. Adv. DrugDel Rev. 42: 29-64 (2000) and U.S. Pat. Nos. 5,762,959, 5,550,178, and 5,578,314.

Encapsulation methods are described in detail in application PCT/US02/41616; herein incorporated by reference.

Implantation or transplantation into a mammal and subsequent monitoring of endocrine function may be carried out according to methods commonly employed for islet transplantation; see, e.g., Ryan et al., Diabetes 50: 710-19 (2001); Peck et al., Ann Med 33: 186-92 (2001); Shapiro et al., N Engl J Med 343 (4): 230-8 (2000); Carlsson et al., Ups J Med Sci 105 (2): 107-23 (2000) and Kuhtreiber, W M, Cell Encapsulation Technology and Therapeutics, Birkhauser, Boston, 1999. Preferred sites of implantation include the peritoneal cavity, the liver, and the kidney capsule. In some aspects a person skilled in the art will be able to determine an appropriate dosage of microcapsules for an intended recipient. In some aspects a person skilled in the art will be able to determine an appropriate dosage of microcapsules or fully differentiated beta cells for an intended recipient. The dosage will depend on the insulin requirements of the recipient. Insulin levels secreted by the microcapsules can be determined immunologically or by amount of biological activity. The recipient's body weight can also be taken into account when determining the dosage. If necessary, more than one implantation can be performed as the recipient's response to the encapsulated cells is monitored. Thus, the response to implantation can be used as a guide for the dosage of encapsulated cells. (Ryan et al., Diabetes 50: 710-19 (2001)) C.

The function of transplanted pancreatic cells in a recipient can be determined by monitoring the response of the recipient to glucose. Implantation of the pancreatic cells can result in control of blood glucose levels. In addition, evidence of increased levels of pancreatic endocrine hormones, insulin, C-peptide, glucagon, and somatostatin can indicate function of the transplanted cells.

The function of encapsulated cells in a recipient can be determined by monitoring the response of the recipient to glucose. Implantation of the encapsulated cells can result in control of blood glucose levels. In addition, evidence of increased levels of pancreatic endocrine hormones, insulin, C-peptide, glucagon, and somatostatin can indicate function of the transplanted encapsulated cells.

One of skill in the art will recognize that control of blood glucose can be monitored in different ways. For example, blood glucose can be measured directly, as can body weight and insulin requirements. Oral glucose tolerance tests can also be given. Renal function can also be determined as can other metabolic parameters. (Soon-Shiong, P. et al., PNAS USA 90: 5843-5847 (1993); Soon-Shiong, P. et al., La7lcet 343: 950-951 (1994)).

The term "insulin producing endocrine pancreatic cells" as used herein refers to cells that produce insulin and secrete insulin in a blood glucose dependent manner.

In another embodiment, the cell population comprising pancreatic cells are isolated (this invention) from a cultured source. The isolated cells are then used for example in further culturing or for microencapsultation according to the microencapsulation method of U.S. Pat. No. 5,762,959.

The term "providing pancreatic function to a mammal in need of such function" refers to a method of producing pancreatic hormones within the body of a mammal unable to produce such hormones on its own. In one embodiment, the pancreatic hormone is selected from the group consisting of insulin, glucagon, somatostatin, pancreatic polypeptide, and ghrelin. In some embodiments, insulin is produced in the body of a diabetic mammal. The pancreatic function is provided by implanting or transplanting insulin producing pancreatic cells, produced by the methods of this disclosure into the mammal. The number of aggregates implanted is an amount sufficient to produce a measurable amount of insulin in the mammal. The insulin can be measured by Western blotting or by other detection methods known to those of skill in the art, including assays for insulin function, such as maintenance of blood glucose levels. Alternatively, insulin can be measured by Elisa assay or Radioimmunoassay.

Insulin can also be measured by detecting C-peptide in the blood. Insulin is cosecreted with C-peptide in equimolar amounts and thus, insulin secretion activity can be measured by detecting C-peptide in the blood. In another preferred embodiment, the provision of pancreatic function is sufficient to decrease or eliminate the dependence of the mammal on insulin produced outside the body.

"Encapsulation" refers to a process where cells are surrounded by a biocompatible acellular material, such as sodium alginate and polylysine. Preferably small molecules, like sugars and low molecular weight proteins, can be taken up from or secreted into an environment surrounding the encapsulated cells. At the same time access to the encapsulated cells by larger molecules and immune cells is limited.

"Implanting" is the grafting or placement of the cells into a recipient. It includes encapsulated cells and non-encapsulated. The cells can be placed subcutaneously, intramuscularly, intraportally or interperitoneally by methods known in the art.

In one aspect, the step of separating is done by fluorescence activated cell sorting. In another aspect, the step of separating is done by panning. In another aspect, the step of separating is done by fluidised bed.

The invention also relates to the use of a DDR1-binding agent to identify or select cells that express DDR1 protein as a cell surface marker. In some aspects the invention relates to the simultaneous or sequential use of a DDR1 binding reagent to identify or select cells that express DDR1 protein as a cell surface marker in combination with one or more additional binding reagents, which are subjected to the same step(s) of analysis as the DDR1 binding reagent. In a specific aspect of the invention, the additional binding reagent is selected from the group consisting of prominin 1 (also known as CD133), and CD49f binding reagent. The invention also relates to the use of DDR1 protein as a cell surface marker to obtain a culture of pancreatic endocrine progenitor cells or pancreatic hormone secreting cell or early endocrine cells. In some aspects the invention relates to the simultaneous or sequential use of DDR1 protein as a cell surface marker to obtain a culture of pancreatic endocrine progenitor cells or pancreatic hormone secreting cell or early endocrine cells in combination with one or more additional binding reagents. In some embodiments, the additional binding reagent may be subjected to the same step(s) of analysis as the DDR1 binding reagent. In a specific aspect of the invention, the additional binding reagent is selected from the group consisting of prominin 1 (also known as CD133), and CD49f binding reagent. In other aspects of the invention the additional binding reagents are selected from the group consisting of Ptprn/IA2, Abcc8/Sur1, and Slc30a8/ZnT-8 binding reagent, which can be used to isolate early and fully differentiated endocrine cells.

The invention also relates to the method of treating type I diabetes by providing pancreatic function to a mammal in need of such function.

In one embodiment compositions comprising pancreatic endocrine cells substantially free of other cell types may be produced. In one aspect of the invention, the expression "substantially free of" is for cell cultures or cell populations to be understood as a cell culture or cell population comprising less than 20% other cell types than pancreatic endocrine progenitor cells in relation to the total number of cells.

In Vitro Protocol Optimisation

In some aspects of the invention, an in vitro culture comprising pancreatic cells is periodically monitored for expression of DDR1. In some aspects of the invention one or more additional markers may be used in combination with DDR1 either simultaneously or sequentially. In some aspects the additional marker is selected from the group consisting of prominin 1 (also known as CD133), and CD49f. Expression of DDR1 include cells that are committed to become endocrine cells but that are at a stage of development prior to, during or after expression of Ngn3 protein.

For optimization of differentiation of embryonic stem cells it is very important to have markers identifying the various stages of development of pancreatic cells towards fully differentiated endocrine cells. DDR1 may alone or in combination be used to pinpoint important and specific stages of cellular differentiation which until now not have been possible to detect using other markers. DDR1 may be used in combination with one or more additional markers.

Cells expressing DDR1 can be identified, enriched, and/or isolated using methods as described above, e.g., FACS or MACS.

Isolation of DDR1+ cells provide the substantial advantage of generating pure cultures of ductal/endocrine progenitor cells, endocrine progenitor cells and/or endocrine progenitor cells, e.g., from an ES cell-derived definitive endodermal cell population. Hereby cultures that can be subjected to further expansion and/or differentiated towards more pure endocrine cell populations may be obtained.

EXAMPLES

Example 1

Bioinformatic Analysis of Mouse Ddr1 and Human DDR1

To investigate the amino acid differences between the three isotypes of DDR1 in human (FIG. 1) and the two isotypes found in mouse (FIG. 2) the amino acid sequence of the proteins were aligned by the use of Clustal W (at http://www.ebi.ac.uk/Tools/clustalw2/index.html). To find the extracellular and transmembrane domains all isotypes were passed through the transmembrane predictor TMHMM Server v. 2.0 at CBS (http://www.cbs.dtu.dk/services/TMHMM/) (data only shown for the longest forms of mouse Ddr1: Isoform 1) and the longest forms of human DDR1: Isoform c). This showed that all three human isotypes had transmembrane domain in the same place, namely amino acid 417-439 (FIG. 1 bold) and the two mouse isotypes had the domain at amino acid 415-437 (FIG. 2 bold). This established that the three human isotypes of DDR1 and the two mouse isotypes of Ddr1 had the same amino acid sequence on the extracellular side, respectively. Specifically the results showed that mouse Ddr1, isoform 1, is a single transmembrane protein with amino acids 1-414 on the extracellular side. In addition the results showed that Human DDR1, isoform c, is a single transmembrane protein with amino acids 1-416 on the extracellular side.

Human DDR1 (isotype c) and mouse Ddr1 (isotype 1) were then passed through posttranslational prediction servers at cbs to obtain information about modifications that could also be bound by DDR1/Ddr1 binding reagents. The results showed that glycation of episilon amino groups of lysines of the mouse DDR1, isotype 1, on the extracellular side was a predicted modification in amino acid position 31. The results showed that glycation of episilon amino groups of lysines of the human DDR1, isotype c, on the extracellular side was a predicted modification in amino acid positions 30 and 243. The results showed that mucin type GalNAc O-glycosylation of mouse DDR1, isotype 1, on the extracellular side was a predicted modification in amino acid positions 377 and 391. The results showed that mucin type GalNAc O-glycosylation of human DDR1, isotype c, on the extracellular side was a predicted modification in amino acid positions 379 and 393. This showed that several posttranslational modifications are predicted.

The results relating to extracellular and transmembrane domains as well as posttranslational prediction and showed that several modifications were present on the extracellular side of DDR1/Ddr1 that can also be used as targets for DDR1/Ddr1 binding reagents. Furthermore, the results showed that the differences between the DDR1/Ddr1 isotypes were only found in the intracellular side and accordingly variation between the isotypes will not affect the extracellular domain by which cells can be identified.

Example 2

Investigation of Isotypes Expressed in e15.5 Mouse Gut

A PCR was performed on cDNA from e15.5 mouse gut tissue (including pancreas, stomach, duodenum and spleen). The PCR was performed under standard conditions (97 degrees for 180 seconds then 35 cycles of 96 degrees for 30 seconds, 55 degrees for 30 seconds and 72 degrees for 30 seconds) with primers flanking the 37 amino acids missing in isoform 2 compared to isoform 1.

The results showed that Ddr1 isoform 1 (911 aa) exhibited higher expression levels than isoform 2 in e15.5 mouse gut. PCR primers located on either side of the sequence coding for the 37 amino acids missing in isoform 2 amplified either a 328 by fragment when isoform 1 was the template or 215 by if isoform 2 was the template. cDNA from e15.5 gut tissue was used as template. From a semi quantitative gel it was observed that both isoforms were expressed in the gut and that isoform 1 was expressed at higher levels than isoform 2.

Two bands are observed corresponding to Ddr1 isoform 1 and 2. Thus both Ddr1 isoforms are expressed in the mouse gut.

Example 3

Investigation of the Expression Pattern of Ddr1 in Mouse

In-situ hybridisation (ISH) for Ddr1 in the mouse pancreas was done by using a digoxigenin labelled cRNA probes generated by in vitro transcription using reagents from Roche according to manufacturer's instruction. Frozen sections were thawed and denatured cRNA probes diluted to 1 ng/µl in hybridization solution were added directly to the sections. The sections were covered with a cover slip and placed in a humidified chamber at 65° C. over night. The slides were washed in wash solution at 65° C. followed by several washes in MABT at room temperature. The sections were blocked for 1 hour and incubated over night with an AP conjugated sheep-anti-DIG (Roche). The sections were washed in MABT and then equilibrated in NTMT. AP activity was visualized with NBT/BCIP in NTMT.

It was observed that the ISH signal for Ddr1 became more and more restricted the older the embryos were. At e12.5 all cells in the pancreas were positive for ISH signal but at e18.5 only what appeared to be the forming endocrine cells were positive.

Immunohistochemistry (IHC) was performed on sections, embryos were fixed in 4% PFA at 4° C. over night, equilibrated in 30% sucrose in PBS and frozen in Tissue-Tek OCT compound. Sections were washed in PBS and blocked for at least 1 hour in 0.5% TNB (PerkinElmer). Primary antibody for Ddr1 (R&D systems, cat: AF2396), Nkx6.1, glucagon and insulin were diluted in 0.5% TNB and applied over night. Secondary antibodies were applied for 1 hour after several washes in PBS and slides were mounted in 20% glycerol. Secondary antibodies were purchased from Jackson ImmunoResearch (Cy3 conjugated donkey-anti-rabbit and donkey-anti-guinea pig and Cy5 conjugated donkey-anti-mouse). Images were collected by confocal microscopy on an LSM 510 META Laser Scanning Microscope (Carl Zeiss) and fluorescent signals were assigned false colours with Zeiss LSM software.

As observed for the ISH signal the expression of Ddr1 became more and more restricted as development progresses, and in the adult pancreas Ddr1 was not readily detectable by IHC. Together these results showed that Ddr1 labelled the endocrine progenitors throughout pancreas development and with varying degree depending on age of embryo, the hormone positive cells.

The results showed that Ddr1 marked the pancreatic endocrine progenitor cell population in the mouse pancreas. Specifically after having analysed e12.5, e15.5, and e18.5 by ISH the results showed that Ddr1 marked all cells in the pancreas early at 12.5, ISH signal is restricted to the middle part at e15.5, and finally at 18.5 the Ddr1 ISH signal ended up in what appeared to be the forming endocrine cells. Specifically using IHC at e15.5 a significant overlap between Ddr1 and Nkx6.1 was observed. Ddr1 did not mark the acinar cells (negative for Nkx6.1). The Nkx6.1 positive cell population at e15.5 comprised the pancreatic endocrine progenitor population and newly formed beta cells but not glucagon producing cells. With a few exceptions cells expressing Ddr1 did not express insulin, glucagon or ghrelin as determined using IHC at e15.5. At e18.5 IHC showed that Ddr1 was expressed in the forming Islet of Langerhans consisting of early endocrine cells and some duct like structures close to the forming islets, and that most of the Nkx6.1 positive cells were positive for Ddr1. Using further IHC at e18.5 for Ddr1, insulin and glucagon revealed that Ddr1 was co-expressed with the early endocrine cells expressing insulin and glucagon but that a few insulin and glucagon cells were negative for Ddr1 and that Ddr1 positive cells were also found in duct-like structures near the forming islet. Specifically in the adult pancreas Ddr1 was not expressed whereas Nkx6.1, insulin and glucagon was readily detected.

At e15.5 Ddr1 showed a striking overlap with Nkx6.1. Cells positive for Nkx6.1 at this time point are likely give rise to endocrine cells and some duct cells in the adult mouse. Thus Ddr1 is labelling the endocrine progenitors, early endocrine cells and most likely some duct cell progenitors. At e18.5 Ddr1 was also co-expressed with Nkx6.1 but compared to e15.5 more cells are Ddr1+/Nkx6.1−. However, hormone positive cells co-expressed Ddr1 to a much higher degree compared to e15.5. This pattern of expression makes Ddr1 excellent as a purification tag for pancreatic endocrine progenitor cells.

Example 4

Localization of Ddr1 in the e15.5 Mouse Pancreas Visualized by Fluorescent Staining Fluorescent stainings were carried out to determine localization of Ddr1 in the e15.5 mouse pancreas. Mouse e15.5 embryos were harvested and fixed over night (O/N) in 4% paraformaldehyde (PFA) in PBS. Tissue was equilibrated in 30% sucrose in PBS and embedded in TissueTech. 8 µm sections were cut and stored at −80° C. Sections were thawed at room temperature (RT), washed in PBS, microwaved in 0.01 M citrate buffer and incubated with 1% $H_2O_2$ in PBS for 30 minutes and subsequently blocked with 0.5% TNB blocking reagent (from Perkin-Elmer). Goat anti-Ddr1 (R&D systems, AF2396) at 1:150, rabbit anti-Ghrelin (C. Tomasetto, 1882) at 1:1000 rabbit anti-Ngn3 (BCBC Abcore, 2369A) at 1:4000, rabbit anti-Ki-67 (NeoMarkers, RB081-0A) at 1:450, and rabbit anti-Pcna (Santa Cruz, sc-7907) at 1:250 were then added and incubated O/N at RT. The following day slides were washed in PBS and biotinylated anti-goat antibody and donkey anti-rabbit-cy5 was added and incubated for 45 minutes. After washing the slides in PBS, streptavidin-HRP was added and incubated for 15 minutes. Subsequently, the slides were washed in PBS. Finally, TSA-cy3 was added to develop the staining and slides were washed in PBS and mounted.

Localization of Ddr1 in the e15.5 mouse embryo was visualized by fluorescent staining, on adjacent sections. Ddr1 as well as Nkx6.1 showed to be strongly and broadly expressed in the central domain of the pancreas that at this time point among other cell types contains endocrine progenitors. Ddr1 and Nkx6.1 were not expressed in the adjacent endoderm, i.e. the duodenum or posterior stomach. More distant from the pancreas Ddr1 was expressed in the anterior stomach, esophagus and parts of the lung as well as in the small intestine. Ddr1 was generally not expressed in the neural tissue apart from some expression in the central part of the neural tube.

Results further showed that approx. 90% of the Ngn3 positive cells co-expressed Ddr1 in the e15.5 pancreas also visualized by fluorescent staining Results further showed that approx. 10-20% of the Ddr1 positive cells in the e15.5 pancreas proliferated as they were positive for Ki-67, which is a marker of cellular proliferation, as visualized by fluorescent staining.

Results further showed that at e15.5 Ddr1 was expressed in nearly all cells of the major pancreatic duct close to the junction of the duct to the duodenum. Notably Ddr1 was only expressed in the pancreas and a sharp boundary of Ddr1 positive cells in the major pancreatic duct and Ddr1 negative cells in the duodenum is observed as visualized by fluorescent staining.

Example 5

Sorting of betaTC3 Cells Using DDR1 via FACS

Ddr1 sorting of live betaTC3 was carried out by FACS. BetaTC3 cells were treated with trypsin and washed. To remove supernatant cells were pelleted by 1400 rpm in 5 minutes at RT in 10 ml tubes. Following this cells were washed in PBS with 0.1% BSA. Primary antibody solution was added and incubated for 45 min at +4° C. Following this cells were washed in PBS with 0.1% BSA. Secondary antibody was added and incubated for 30 min at +4° C. Cells were washed 3×5 min in PBS with 0.1% BSA (using 1.8 ml). Finally, cells fixed for 45 minutes in Lillys fixative washed in PBS with 0.1% BSA and assayed by FACS. Specifically, mouse anti-Ddr1 (R&D Systems, MAB2396) was used 1:50 and developed with donkey anti-mouse-cy2 (Jackson ImmunoResearch) (1:300).

Performing FACS of stained betaTC3 cells that had been incubated only with secondary donkey anti-mouseCy2 antibody resulted in some fluorescence signal. Addition of the primary mouse IgG2a isotype control antibody resulted in almost the same fluorescence as for secondary antibody alone (i.e. background). However, addition of mouse anti-Ddr1 anti-body resulted in a marked increase in fluorescence, demonstrating that the Ddr1 protein can be used as tag in FACS.

ES cell can be differentiated to become pancreatic cells, but many non-pancreatic cells will also be present in the culture e.g. contaminating endodermal cells (posterior stomach and duodenum), differentiated neuronal cells and mesenchymal cells. By sorting such a mix of cells into populations that are positive for Ddr1 or negative for Ddr1, e.g., by FACS sorting (as it was done for betaTC3 cells), the ductal/endocrine progenitors, endocrine progenitor, and/or early endocrine cells of the pancreas will be purified from the other cells. It should also be noted that among the different pancreatic cell types (acinar, duct and endocrine) the acinar cells will be in the Ddr1 negative population. Thus Ddr1 can also be used at a tag to purify to ductal/endocrine progenitors, endocrine progenitor, and/or early endocrine cells of the pancreas from the other cell types in the pancreas. However, carrying out a double sorting using other markers like CD133 and CD49f might further increase the yield of the wanted cells.

Example 6

Sorting of Mouse Embryonic Pancreatic Cells Using DDR1 via FACS

The pancreas from several e15.5 mouse embryos were micro dissected. To obtain single cells the tissue was trypsinized for 5 min. at 36° C. at 1400 rpm with pipetting from time to time. Cells were then re-suspended in 10 ml media with out serum. To wash out trypsin cells were washed three times in 10 ml media without serum and re-incubated in media with out for 1.5 hours in a cell incubator. Hereafter cells were washed in 10 ml of PBS with 0.1% BSA and split into six tubes. The 1st tube received mouse anti-Ddr1 (R&D Systems, MAB2396) antibody at 10 µg/ml. The 2nd tube received isotype (IgG2a) negative control antibody at 10 µg/ml. The 3rd tube received mouse anti-Ddr1 (R&D Systems, MAB2396) anti-body at 2.5 µg/ml. The 4th tube received isotype (IgG2a) negative control antibody, 2.5 µg/ml. The 5th and 6th tube did not receive any antibody. Cells were then incubated for 45 minutes at 4° C., and tubes were washed in PBS with 0.1% BSA. Secondary donkey anti-mouse-cy2 antibody 1:300 was added to all tubes except for tube 6. Cells were then incubated for 30 minutes at 4° C. Hereafter cells were washed with PBS with 0.1% BSA and finally cells were fixed for 30 minutes in Lilly's fixative and then washed in PBS with 0.1% BSA and analyzed on a FACS.

The results are shown in FIG. 4. FIG. 4A shows the result using mouse anti-Ddr1 as primary antibody at 10 µg/ml. FIG. 4B shows the result using isotype (IgG2a) negative control as primary antibody at 10 µg/ml. It was observed that specific Ddr1 antibody results in a clear labelling of a subpopulation of cells. Thus Ddr1 can be used in FACS on primary mouse pancreatic cells. This shows that Ddr1 binding reagent can be used to isolate ductal/endocrine cells, endocrine progenitor cells, and/or early endocrine cells.

Example 7

Detection of Insulin Production in Fetal Pancreatic-Derived Cells Isolated via DDR1 Using FACS The aim of the experiment is to determine what cell types the Ddr1 positive cells from an e15.5 pancreas give rise to.

Cells from e15.5 are prepared and stained for Ddr1 as described in Example 6 with the following modifications: Mouse anti-Ddr1 (R&D Systems, MAB2396) antibody is used at 10 ug/ml. After secondary antibody and wash cells are not fixed but sorted live on a FACSArian into two tubes containing DMEM/F12+10% FCS+P/S. The Ddr1 positive cells are sorted into one tube. The Ddr1 negative cells are sorted into another tube. Hereafter cells are implanted under the kidney capsule as described by Kroon, E. et al. (2008), Nat Biotechnol, 2008 Feb. 20, [Epub ahead of print]. After in vivo maturation under the kidney capsule for 30-60 days or more the transplanted cells are harvested and fixed in Lilly's fixative, embedded and sectioned. Sections of the implant are stained for mouse anti-insulin (Biolabs, HUI-18) 1:100, mouse anti-glucagon (Biolabs, Glu-001) 1:100 and rabbit-anti-amylase (Sigma, A 8273) 1:500, rabbit anti-Nkx6.1 (Hagedorn, #174.4 1:700), Gt-Pdx1 (Chris Wright, 1:10.000), rabbit anti-somatostatin, 1:500 (Dako, A0566), rabbit anti-PP, 1:300 (Dako, A0169); goat anti-ghrelin, 1:300 (Santa Cruz Biotechnology, SC-10368); rabbit anti-C-peptide, 1:200 (Acris, BP302). To detect the primary antibodies secondary-cy2, cy3 and cy5 antibodies will be used.

It is expected that the implants with the Ddr1 positive population will comprise insulin/glucagon expressing cells and that the implants with the Ddr1 negative cells will comprise amylase positive cells.

Example 8

Detection of Insulin Production in ES-Derived Cells Isolated via DDR1 Using FACS The aim of the experiment is to determine what cell types the Ddr1 positive cells from an embryonic stem cell give rise to.

Embryonic stem cells may be isolated and differentiated according to the protocol described by Kroon, E. et al. (2008), Nat Biotechnol, 2008 Feb. 20, [Epub ahead of print] until stage 4 is reached. Then ES-derived cells are prepared and stained for Ddr1 as described in Example 6 with the following modifications: Mouse anti-Ddr1 (R&D Systems, MAB2396) antibody is used at 10 ug/ml. After secondary antibody and wash cells are not fixed but sorted live on a FACSArian into two tubes containing DMEM/F12+10% FCS+P/S. The Ddr1 positive cells are sorted into one tube. The Ddr1 negative cells are sorted into another tube. Hereafter cells are implanted under the kidney capsule as described by Kroon, E. et al. (2008), Nat Biotechnol, 2008 Feb. 20, [Epub ahead of print]. Transplant is treated and stained by IHC according to Example 7.

It is expected that the implants with the Ddr1 positive population will comprise insulin/glucagon expressing cells and that the implants with the Ddr1 negative cells will comprise amylase positive cells.

Example 9

Optimisation of In Vitro Protocol for the Differentiation of Stem Cells by Quantification of the Expression DDR1 and Optionally Ngn3

For optimization of differentiation of stem cells, such as ES cells, it is very important to have markers identifying the various stages of development of pancreatic cells into fully differentiated endocrine cells (see FIG. 3). DDR1 may be used alone or in combination with one or more additional markers to pinpoint important and specific stages of cellular differentiation which until now have not been possible to detect using other markers.

In some aspects the method of optimisation of an in vitro protocol for the differentiation of stem cells is a method of screening for optimal culture conditions.

In some aspects the method of optimisation of an in vitro protocol for the differentiation of stem cells comprises of the steps of:
a) quantifying DDR1 positive cells by 1) contacting a population of cells with a DDR1 binding reagent and 2) determining the quantity of cells exhibiting DDR1 as a cell surface marker (DDR1 positive cells);
b) optionally separating the cells that bind the DDR1 binding reagent in a fraction of DDR1 positive cells from cells that do not bind the DDR1 binding reagent;
c) optionally expanding the numbers of pancreatic cells selected from the group consisting of ductal/endocrine progenitor cells, endocrine progenitor cells, and early endocrine cells by culturing the population of cells comprising DDR1 positive cells under conditions which facilitate expansion of the cell type(s) obtained;
d) culturing the population of cells comprising DDR1 positive cells under conditions which facilitate their differentiation into pancreatic cells selected from the group consisting of ductal/endocrine progenitor cells, endocrine progenitor cells, early endocrine cells, and fully differentiated endocrine cells;

e) optionally expanding the numbers of pancreatic cells selected from the group consisting of ductal/endocrine progenitor cells, endocrine progenitor cells, and early endocrine cells by culturing the population of cells comprising DDR1 positive cells under conditions which facilitate expansion of the cell type(s) obtained;

f) quantifying DDR1 positive cells by 1) contacting a population of cells with a DDR1 binding reagent and 2) determining the quantity of cells exhibiting DDR1 as a cell surface marker (DDR1 positive cells);

g) determining whether the quantity of DDR1 positive cells in step f) is larger than the quantity of DDR1 positive cells in step a);

h) optionally separating the cells that bind the DDR1 binding reagent in a fraction of DDR1 positive cells from cells that do not bind the DDR1 binding reagent;

i) optionally introducing an adjustment of culture conditions in order to increase the quantity of DDR1 positive cells by varying conditions which affect differentiation, such as 1) concentration or combination of differentiation factors, 2) concentration or composition of growth media, 3) concentration or composition of supplements to the growth media, 4) time of incubation, and/or 5) oxygen tension;

j) optionally separating the cells that bind the DDR1 binding reagent in a fraction of DDR1 positive cells from cells that do not bind the DDR1 binding reagent;

k) repeating the sequence of steps a) to h) until a satisfactory quantity of DDR1 positive cells has been obtained.

In some aspects determination of the quantity DDR1 positive cells may be carried out using an automated staining system, e.g., with fluorescence detection.

Identification of ductal/endocrine progenitor cells, endocrine progenitor cells, and/or early endocrine cells may be achieved by contacting the cell population with a DDR1 binding reagent, optionally in combination with an additional binding reagent for another endodermal marker (e.g., Pdx1 binding reagent) and evaluating the staining. The choice of binding reagent may depend on the composition of the cells culture, such as whether neural cells are present in the cell culture because DDR1 will mark endoderm and not neural cells innervating the pancreas. By co-staining for Ngn3 and DDR1 cells that are double positive can be grouped into the endocrine progenitor group. This analysis may be carried out using a method such as FACS, MACS, IHC, or panning.

Embodiments of the Invention

1. A method of identification of pancreatic cells comprising cells selected from the group consisting of ductal/endocrine progenitor cells, endocrine progenitor cells, and early endocrine cells, the method comprising contacting a cell population comprising pancreatic cells with a DDR1 binding reagent.

2. A method of obtaining a culture of pancreatic cells comprising cells selected from the group consisting of ductal/endocrine progenitor cells, pancreatic endocrine progenitor cells, and early endocrine cells comprising: contacting a cell population comprising pancreatic cells with a DDR1 binding reagent and separating the cells that binds the DDR1 binding reagent in a fraction of DDR1 positive cells from cells that do not bind the DDR1 binding reagent.

3. A method of obtaining a culture of pancreatic cells comprising cells selected from the group consisting of ductal/endocrine progenitor cells, endocrine progenitor cells, and early endocrine cells comprising: obtaining cells purified according to the method of embodiment 2 and then subsequently culturing the obtained cells under conditions which facilitate their differentiation into pancreatic cells comprising cells selected from the group consisting of ductal/endocrine progenitor cells, endocrine progenitor cells, early endocrine cells, and fully differentiated endocrine cells.

4. A method of expanding the numbers of pancreatic cells selected from the group consisting of ductal/endocrine progenitor cells, endocrine progenitor cells, and early endocrine cells comprising: obtaining cells purified according to embodiment 2 and then subsequently culturing the obtained cells under conditions which facilitate expansion of the cell type(s) obtained.

5. A method of expanding the numbers of pancreatic cells selected from the group consisting of ductal/endocrine progenitor cells, endocrine progenitor cells, and early endocrine cells comprising: obtaining cells purified and expanded according to embodiment 4 and then subsequently culturing the obtained cells under conditions which facilitates differentiation of the cells into pancreatic cells selected from the group consisting of ductal/endocrine progenitor cells, endocrine progenitor cells, early endocrine cells, and fully differentiated endocrine cells.

6. A method of providing pancreatic endocrine function to a mammal deficient in its production of at least one pancreatic hormone wherein cells are obtained by the method according to any one of embodiments 1-5, the method further comprising the steps of: implanting into the mammal the obtained cells in an amount sufficient to produce a measurable amount of at least one pancreatic hormone in the mammal.

7. The method according to embodiment 6, wherein the amount of pancreatic hormone is determined no earlier than the day after the transplantation or after in vivo maturation, such as at least 1, 2, 3 or 4 weeks after transplantation.

8. The method according to embodiment 6 or 7, wherein said at least one pancreatic hormone is insulin.

9. The method according to any of embodiments 6-8, wherein the mammal is a human being.

10. The method according to any one of embodiments 1-9, wherein said at least one pancreatic hormone is selected from the group consisting of insulin, glucagon, somatostatin, and pancreatic polypeptide and ghrelin.

11. A method of quantifying DDR1 positive cells by a) contacting the cells with a DDR1 binding reagent; and b) determining the quantity of cells that exhibit DDR1 as a cell surface marker (DDR1 positive cells).

12. A method for the optimisation of an in vitro protocol, wherein the number of DDR1 expressing cells (DDR1 positive cells) is periodically monitored.

13. The method according to any one of embodiments 1-12, wherein one or more additional binding reagents are used in combination with the DDR1 binding reagent either simultaneously or sequentially.

14. The method according to embodiment 13, wherein an additional binding reagent is selected from the group consisting of prominin 1 (also known as CD133), and CD49f binding reagents.

15. The method according to any one of the embodiments 1-14, wherein the DDR1 positive cells are differentiated further into insulin producing cells, optionally together with cells differentiated further into cells selected from the group consisting of glucagon, somatostatin, pancreatic polypeptide and ghrelin producing cells.

16. The method according to any one of the embodiments 1-15, wherein the cell population comprising pancreatic cells is obtained from a pancreas.

17. The method according to any one of the embodiments 1-15, wherein the cell population comprising pancreatic cells is a somatic cell population.
18. The method according to embodiment 17, wherein the somatic cell population has been induced to de-differentiate into pluripotent cells such as ES like-cells, e.g. IPS cells, epiblast stem cells or germ cells.
19. The method according to any one of the embodiments 1-15, wherein the cell population comprising pancreatic cells is obtained from pluripotent cells such as ES cells.
20. The method according to any one of the preceding embodiments, wherein the cell population comprising pancreatic cells is of vertebrate origin.
21. The method according to any one of the preceding embodiments, wherein the cell population comprising pancreatic cells is of mammalian origin.
22. The method according to any one of the preceding embodiments, wherein the cell population comprising pancreatic cells is of human origin.
23. The method according to any one of the preceding embodiments, wherein the cell population comprising pancreatic cells is of mouse origin.
24. The method according to any one of the preceding embodiments, wherein the cell population comprising pancreatic cells is of rat origin.
25. The method according to embodiment 20, wherein the cell population comprising pancreatic cells is of chicken origin.
26. The method according to any of embodiments 20-25, wherein the cell population has been differentiated to the pancreatic endocrine lineage.
27. The method according to embodiment 26, wherein differentiation of the cells comprises culturing the cells in a medium comprising one or more differentiation factor(s).
28. The method according to any one of the embodiments 1-27, wherein the cell population comprising pancreatic cells is a beta cell-positive fraction.
29. The method according to any one of the embodiments 1-27, wherein the cell population comprising pancreatic cells is a ptprn/IA2-positive fraction.
30. The method according to any one of the embodiments 1-27, wherein the cell population comprising pancreatic cells is an Abcc8/Sur1-positive fraction.
31. The method according to any one of the embodiments 1-27, wherein the cell population comprising pancreatic cells is a Slc30a8/ZnT-8-positive fraction.
32. The method according to any one of the embodiments 1-27, wherein the culture of pancreatic endocrine cells obtained by the method according to any of the above embodiments is further separated in a beta cell-positive fraction.
33. The method according to any one of the embodiments 1-27, wherein the culture of pancreatic endocrine cells obtained by the method according to any of the above embodiments is further separated in a Ptprn/IA2-positive fraction.
34. The method according to any one of the embodiments 1-27, wherein the culture of pancreatic endocrine cells obtained by the method according to any of the above embodiments is further separated in an Abcc8/Sur1-positive fraction.
35. The method according to any one of the embodiments 1-27, wherein the culture of pancreatic endocrine cells obtained by the method according to any of the above embodiments is further separated in a Slc30a8/ZnT-8-positive fraction.
36. The method according to any one of the preceding embodiments, wherein the DDR1 binding reagent is an antibody that specifically binds to DDR1.
37. The method according to any one of the preceding embodiments, wherein the step of separating or monitoring is done by fluorescence activated cell sorting.
38. The method according to any one of the preceding embodiments, wherein the step of separating or monitoring is done by magnetic activated cell sorting.
39. The method according to any one of the preceding embodiments, wherein the step of separating is done by panning.
40. The method according to any one of the preceding embodiments, wherein the cells are endocrine progenitor cells.
41. An isolated cell selected from the group consisting of ductal/endocrine progenitor cells, endocrine progenitor cells, early endocrine cells obtained by a method as defined in any of the embodiments 1-40 and fully differentiated endocrine cells obtained by a method as defined in any of the embodiments 3 or 5-40.
42. An isolated endocrine progenitor cell obtained by a method as defined in any of the embodiments 1-40.
43. An isolated fully differentiated endocrine cell obtained by a method as defined in any of the embodiments 3 or 5-40.
44. A composition comprising isolated cells selected from one or more cells from the group consisting of ductal/endocrine progenitor cells, endocrine progenitor cells, early endocrine cells obtained by a method as defined in any of the embodiments 1-40 and fully differentiated endocrine cells obtained by a method as defined in any of the embodiments 3 or 5-40.
45. Use of a DDR1 binding reagent to identify or select cells that express DDR1 protein as a cell surface marker.
46. Use of DDR1 protein as a cell surface marker to obtain a culture of pancreatic endocrine cells.
47. Use according to embodiment 46, wherein one or more further cell surface markers are used simultaneously or sequentially to obtain a culture of pancreatic endocrine cells.
48. Use according to embodiment 47, wherein a further cell surface marker is selected from the group consisting of prominin 1 (also known as CD133), and CD49f.

Further Embodiments of the Invention

1. A method of obtaining a culture of pancreatic endocrine progenitor cells and/or early endocrine cells and/or pancreatic hormone secreting cells comprising: contacting a cell population comprising pancreatic cells with a DDR1 binding reagent and separating the cells that binds the DDR1 binding reagent in a fraction of DDR1 positive cells from cells that do not bind the DDR1 binding reagent.
2. A method of obtaining a culture of pancreatic endocrine cells and/or pancreatic hormone secreting cells and/or early endocrine cells and/or mature endocrine cells comprising: obtaining cells purified according to the method of embodiment 1 and then subsequently culturing the obtained cells under conditions which facilitate their differentiation into pancreatic endocrine cells and/or pancreatic hormone secreting cells and/or early endocrine cells and/or mature endocrine cells.
3. A method of expanding the numbers of pancreatic endocrine progenitor cells and/or early endocrine cells and/or pancreatic hormone secreting cells comprising: obtaining cells purified according to embodiment 1 and then subsequently culturing the obtained cells under conditions which facilitate expansion of the cell type(s) obtained.

4. A method of expanding the numbers of pancreatic endocrine cells and/or pancreatic hormone secreting cells and/or early endocrine cells and/or mature endocrine cells comprising: obtaining cells purified and expanded according to embodiment 3 and then subsequently culturing the obtained cells under conditions which facilitates differentiation of the cells into pancreatic endocrine cells and/or pancreatic hormone secreting cells and/or early endocrine cells and/or mature endocrine cells 5. A method of providing pancreatic endocrine function to a mammal deficient in its production of at least one pancreatic hormone wherein cells are obtained by the method according to any one of embodiments 1-4, the method further comprising the steps of implanting into the mammal the obtained cells in an amount sufficient to produce a measurable amount of at least one pancreatic hormone in the mammal.

6. The method according to any one of embodiments 1-5, wherein said at least one pancreatic hormone is selected from the group consisting of insulin, glucagon, somatostatin, and pancreatic polypeptide.

7. A method of monitoring a culture of cells comprising pancreatic cells by a) contacting the cells with a DDR1 binding reagent; and b) determining the quantity of cells that exhibit DDR1 as a cell surface marker (DDR1 positive cells).

8. The method according to any one of the embodiments 1-7, wherein the DDR1 positive cells are differentiated further into insulin producing cells, optionally together with cells differentiated further into glucagon and/or somatostatin and/or pancreatic polypeptide producing cells.

9. The method according to any one of the embodiments 1-7, wherein the cell population comprising pancreatic cells is obtained from a pancreas.

10. The method according to any one of the embodiments 1-7, wherein the cell population comprising pancreatic cells is a somatic cell population.

11. The method according to embodiment 10, wherein the somatic cell population has been induced to de-differentiate into pluripotent-like cells such as ES like-cells.

12. The method according to any one of the embodiments 1-7, wherein the cell population comprising pancreatic cells is pluripotent-like cells such as ES like-cells.

13. The method according to any one of the preceding embodiments, wherein the cell population comprising pancreatic cells is of mammalian origin.

14. The method according to any one of the preceding embodiments, wherein the cell population comprising pancreatic cells is of human origin.

15. The method according to any embodiment 13 or 14, wherein the cell population has been differentiated to the pancreatic endocrine lineage.

16. The method according to embodiment 15, wherein differentiation of the cells comprises culturing the cells in a medium comprising one or more differentiation factor(s).

17. The method according to any one of the embodiments 1-16, wherein the cell population comprising pancreatic cells is a Ptprn-positive fraction.

18. The method according to any one of the embodiments 1-16, wherein the cell population comprising pancreatic cells is a Abcc8-positive fraction.

19. The method according to any one of the embodiments 1-16, wherein the cell population comprising pancreatic cells is a Glut-2/1-positive fraction.

20. The method according to any one of the embodiments 1-16, wherein the cell population comprising pancreatic cells is a Slc30a8-positive fraction.

21. The method according to any one of the embodiments 1-16, wherein the culture of pancreatic endocrine cells obtained by the method according to any of the above embodiments is further separated in a Ptprn-positive fraction.

22. The method according to any one of the embodiments 1-16, wherein the culture of pancreatic endocrine cells obtained by the method according to any of the above embodiments is further separated in a Abcc8-positive fraction.

23. The method according to any one of the embodiments 1-16, wherein the culture of pancreatic endocrine cells obtained by the method according to any of the above embodiments is further separated in a Glut-2/1-positive fraction.

24. The method according to any one of the embodiments 1-16, wherein the culture of pancreatic endocrine cells obtained by the method according to any of the above embodiments is further separated in a Slc30a8-positive fraction.

25. The method according to any one of the preceding embodiments, wherein the DDR1 binding reagent is an antibody that specifically binds to the DDR1 protein.

26. The method according to any one of the preceding embodiments, wherein the step of separating is done by fluorescence activated cell sorting.

27. The method according to any one of the embodiments 1-26, wherein the step of separating is done by panning.

28. Use of a DDR1-binding agent to identify or select cells that express DDR1 protein as a cell surface marker.

29. Use of DDR1 protein as a cell surface marker to obtain a culture of pancreatic endocrine cells.

30. The method of embodiment 6, wherein said at least one pancreatic hormone is insulin.

31. The method according to embodiment 30, wherein the mammal is a human being.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention described herein was made through support by a grant (#5U01-DK072473) from NIH/NIDDK through Vanderbilt University.

The invention claimed is:

1. A method of identification of pancreatic cells comprising cells selected from the group consisting of ductal/endocrine progenitor cells, endocrine progenitor cells, and early endocrine cells, the method comprising contacting a cell population comprising pancreatic cells with a DDR1 (Discoidin Domain Receptor family, member 1) binding reagent and detecting cells that bind the DDR1 binding reagent.

2. A method of obtaining a culture of pancreatic cells comprising cells selected from the group consisting of ductal/endocrine progenitor cells, pancreatic endocrine progenitor cells, and early endocrine cells comprising: contacting a cell population comprising pancreatic cells with a DDR1 binding reagent and separating the cells that binds bind the DDR1 binding reagent in a fraction of DDR1 positive cells from cells that do not bind the DDR1 binding reagent.

3. The method of claim 2, comprising the subsequent step of culturing the obtained cells under conditions which facilitate their differentiation into pancreatic cells comprising cells selected from the group consisting of ductal/endocrine progenitor cells, endocrine progenitor cells, early endocrine cells, and fully differentiated endocrine cells.

4. The method of claim 2, comprising the subsequent step of culturing the obtained cells under conditions which facilitate expansion of the pancreatic cells obtained.

5. The method of claim 4, further comprising the subsequent steps of obtaining the cells after expansion and culturing the obtained cells under conditions which facilitates differentiation of the cells into pancreatic cells selected from the group consisting of ductal/endocrine progenitor cells, endocrine progenitor cells, early endocrine cells, and fully differentiated endocrine cells.

6. The method of providing pancreatic endocrine function to a mammal deficient in its production of at least one pancreatic hormone wherein cells are obtained by the method according to claim 5, the method further comprising the steps of: implanting into the mammal the obtained cells in an amount sufficient to produce a measurable amount of at least one pancreatic hormone in the mammal.

7. A method of quantifying DDR1 positive cells in an in vitro cell culture comprising pancreatic cells, comprising the steps of a) contacting the cell culture comprising pancreatic cells with a DDR1 binding reagent; and b) determining the quantity of cells that exhibit DDR1 as a cell surface marker (DDR1 positive cells).

8. The method of claim 7, wherein the number of DDR1 positive cells is periodically monitored.

9. The method of claim 1, wherein the DDR1 binding reagent is an antibody that specifically binds to DDR1.

10. The method of claim 1, wherein the cell population comprises pancreatic cells is selected from the group consisting of a cell population obtained from a pancreas, a somatic cell population, and a cell population obtained from pluripotent cells.

11. The method of claim 10, wherein the pluripotent cells are embryonic stem cells.

12. The method of claim 1, wherein the cell population comprising pancreatic cells is of human origin.

13. The method of claim 12, wherein the cell population comprising pancreatic cells has been differentiated into the pancreatic endocrine lineage.

14. The method of claim 1, wherein the cells are endocrine progenitor cells.

15. The method of claim 2, wherein the DDR1 positive cells are further differentiated into insulin producing cells.

16. The method of claim 2, wherein the DDR1 positive cells are further differentiated into insulin producing cells and at least one of glucagon producing cells, somatostatin producing cells, pancreatic polypeptide producing cells or ghrelin producing cells.

17. The method of claim 3, wherein the pancreatic endocrine cells obtained is further separated in a beta cell-positive fraction.

* * * * *

UNITED STATES PATENT AND TRADEMARK OFFICE
CERTIFICATE OF CORRECTION

| | | |
|---|---|---|
| PATENT NO. | : 8,551,779 B2 | |
| APPLICATION NO. | : 12/810960 | |
| DATED | : October 8, 2013 | |
| INVENTOR(S) | : Jacob Hald et al. | |

It is certified that error appears in the above-identified patent and that said Letters Patent is hereby corrected as shown below:

In the Claims:

At column 63, line number 27, delete "binds".

Signed and Sealed this
Thirty-first Day of December, 2013

Margaret A. Focarino
*Commissioner for Patents of the United States Patent and Trademark Office*

SEQUENCE LISTING

<160> NUMBER OF SEQ ID NOS: 5

<210> SEQ ID NO 1
<211> LENGTH: 876
<212> TYPE: PRT
<213> ORGANISM: Homo sapiens

<400> SEQUENCE: 1

Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Arg
                20                  25                  30

Tyr Ala Leu Gly Met Gln Asp Arg Thr Ile Pro Asp Ser Asp Ile Ser
                35                  40                  45

Ala Ser Ser Ser Trp Ser Asp Ser Thr Ala Ala Arg His Ser Arg Leu
            50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                            85                  90                  95

Val Ala Leu Val Gly Thr Gln Gly Arg His Ala Gly Gly Leu Gly Lys
                100                 105                 110

Glu Phe Ser Arg Ser Tyr Arg Leu Arg Tyr Ser Arg Asp Gly Arg Arg
            115                 120                 125

Trp Met Gly Trp Lys Asp Arg Trp Gly Gln Glu Val Ile Ser Gly Asn
        130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
                180                 185                 190

Ser Tyr Thr Ala Pro Val Gly Gln Thr Met Tyr Leu Ser Glu Ala Val
            195                 200                 205

Tyr Leu Asn Asp Ser Thr Tyr Asp Gly His Thr Val Gly Gly Leu Gln
        210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

```
Val Asn Asn Ser Ser Pro Ala Leu Gly Gly Thr Phe Pro Ala Pro
    370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu
        420                 425                 430

Ile Ile Ala Leu Met Leu Trp Arg Leu His Trp Arg Leu Leu Ser
        435                 440                 445

Lys Ala Glu Arg Arg Val Leu Glu Glu Glu Leu Thr Val His Leu Ser
    450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Tyr Ser Gly Asp Tyr Met Glu
                500                 505                 510

Pro Glu Lys Pro Gly Ala Pro Leu Leu Pro Pro Pro Gln Asn Ser
    515                 520                 525

Val Pro His Tyr Ala Glu Ala Asp Ile Val Thr Leu Gln Gly Val Thr
530                 535                 540

Gly Gly Asn Thr Tyr Ala Val Pro Ala Leu Pro Pro Gly Ala Val Gly
545                 550                 555                 560

Asp Gly Pro Pro Arg Val Asp Phe Pro Arg Ser Arg Leu Arg Phe Lys
                565                 570                 575

Glu Lys Leu Gly Glu Gly Gln Phe Gly Glu Val His Leu Cys Glu Val
            580                 585                 590

Asp Ser Pro Gln Asp Leu Val Ser Leu Asp Phe Pro Leu Asn Val Arg
    595                 600                 605

Lys Gly His Pro Leu Leu Val Ala Val Lys Ile Leu Arg Pro Asp Ala
    610                 615                 620

Thr Lys Asn Ala Arg Asn Asp Phe Leu Lys Glu Val Lys Ile Met Ser
625                 630                 635                 640

Arg Leu Lys Asp Pro Asn Ile Ile Arg Leu Leu Gly Val Cys Val Gln
                645                 650                 655

Asp Asp Pro Leu Cys Met Ile Thr Asp Tyr Met Glu Asn Gly Asp Leu
                660                 665                 670

Asn Gln Phe Leu Ser Ala His Gln Leu Glu Asp Lys Ala Ala Glu Gly
        675                 680                 685

Ala Pro Gly Asp Gly Gln Ala Ala Gln Gly Pro Thr Ile Ser Tyr Pro
    690                 695                 700

Met Leu Leu His Val Ala Ala Gln Ile Ala Ser Gly Met Arg Tyr Leu
705                 710                 715                 720

Ala Thr Leu Asn Phe Val His Arg Asp Leu Ala Thr Arg Asn Cys Leu
                725                 730                 735

Val Gly Glu Asn Phe Thr Ile Lys Ile Ala Asp Phe Gly Met Ser Arg
                740                 745                 750

Asn Leu Tyr Ala Gly Asp Tyr Tyr Arg Val Gln Gly Arg Ala Val Leu
            755                 760                 765

Pro Ile Arg Trp Met Ala Trp Glu Cys Ile Leu Met Gly Lys Phe Thr
    770                 775                 780

Thr Ala Ser Asp Val Trp Ala Phe Gly Val Thr Leu Trp Glu Val Leu
```

```
                785                 790                 795                 800

Met Leu Cys Arg Ala Gln Pro Phe Gly Gln Leu Thr Asp Glu Gln Val
            805                 810                 815

Ile Glu Asn Ala Gly Glu Phe Phe Arg Asp Gln Gly Arg Gln Val Tyr
            820                 825                 830

Leu Ser Arg Pro Pro Ala Cys Pro Gln Gly Leu Tyr Glu Leu Met Leu
            835                 840                 845

Arg Cys Trp Ser Arg Glu Ser Glu Gln Arg Pro Pro Phe Ser Gln Leu
            850                 855                 860

His Arg Phe Leu Ala Glu Asp Ala Leu Asn Thr Val
865                 870                 875

<210> SEQ ID NO 2
<211> LENGTH: 919
<212> TYPE: PRT
<213> ORGANISM: Homo sapiens

<400> SEQUENCE: 2

Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
```

-continued

```
              290                 295                 300
Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
                340                 345                 350

Ala Gly Pro Trp Leu Leu Phe Ser Glu Ile Ser Phe Ile Ser Asp Val
                355                 360                 365

Val Asn Asn Ser Ser Pro Ala Leu Gly Gly Thr Phe Pro Pro Ala Pro
370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Leu Leu Leu Leu Leu
                420                 425                 430

Ile Ile Ala Leu Met Leu Trp Arg Leu His Trp Arg Arg Leu Leu Ser
        435                 440                 445

Lys Ala Glu Arg Arg Val Leu Glu Glu Glu Leu Thr Val His Leu Ser
450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Leu Leu Leu Ser Asn Pro Ala
                500                 505                 510

Tyr Arg Leu Leu Leu Ala Thr Tyr Ala Arg Pro Pro Arg Gly Pro Gly
        515                 520                 525

Pro Pro Thr Pro Ala Trp Ala Lys Pro Thr Asn Thr Gln Ala Tyr Ser
        530                 535                 540

Gly Asp Tyr Met Glu Pro Glu Lys Pro Gly Ala Pro Leu Leu Pro Pro
545                 550                 555                 560

Pro Pro Gln Asn Ser Val Pro His Tyr Ala Glu Ala Asp Ile Val Thr
                565                 570                 575

Leu Gln Gly Val Thr Gly Gly Asn Thr Tyr Ala Val Pro Ala Leu Pro
                580                 585                 590

Pro Gly Ala Val Gly Asp Gly Pro Pro Arg Val Asp Phe Pro Arg Ser
        595                 600                 605

Arg Leu Arg Phe Lys Glu Lys Leu Gly Glu Gly Gln Phe Gly Glu Val
        610                 615                 620

His Leu Cys Glu Val Asp Ser Pro Gln Asp Leu Val Ser Leu Asp Phe
625                 630                 635                 640

Pro Leu Asn Val Arg Lys Gly His Pro Leu Leu Val Ala Val Lys Ile
                645                 650                 655

Leu Arg Pro Asp Ala Thr Lys Asn Ala Ser Phe Ser Leu Phe Ser Arg
                660                 665                 670

Asn Asp Phe Leu Lys Glu Val Lys Ile Met Ser Arg Leu Lys Asp Pro
                675                 680                 685

Asn Ile Ile Arg Leu Leu Gly Val Cys Val Gln Asp Asp Pro Leu Cys
        690                 695                 700

Met Ile Thr Asp Tyr Met Glu Asn Gly Asp Leu Asn Gln Phe Leu Ser
705                 710                 715                 720
```

-continued

```
Ala His Gln Leu Glu Asp Lys Ala Glu Gly Ala Pro Gly Asp Gly
            725                 730                 735

Gln Ala Ala Gln Gly Pro Thr Ile Ser Tyr Pro Met Leu Leu His Val
        740                 745                 750

Ala Ala Gln Ile Ala Ser Gly Met Arg Tyr Leu Ala Thr Leu Asn Phe
    755                 760                 765

Val His Arg Asp Leu Ala Thr Arg Asn Cys Leu Val Gly Glu Asn Phe
770                 775                 780

Thr Ile Lys Ile Ala Asp Phe Gly Met Ser Arg Asn Leu Tyr Ala Gly
785                 790                 795                 800

Asp Tyr Tyr Arg Val Gln Gly Arg Ala Val Leu Pro Ile Arg Trp Met
                805                 810                 815

Ala Trp Glu Cys Ile Leu Met Gly Lys Phe Thr Thr Ala Ser Asp Val
            820                 825                 830

Trp Ala Phe Gly Val Thr Leu Trp Glu Val Leu Met Leu Cys Arg Ala
        835                 840                 845

Gln Pro Phe Gly Gln Leu Thr Asp Glu Gln Val Ile Glu Asn Ala Gly
    850                 855                 860

Glu Phe Phe Arg Asp Gln Gly Arg Gln Val Tyr Leu Ser Arg Pro Pro
865                 870                 875                 880

Ala Cys Pro Gln Gly Leu Tyr Glu Leu Met Leu Arg Cys Trp Ser Arg
                885                 890                 895

Glu Ser Glu Gln Arg Pro Pro Phe Ser Gln Leu His Arg Phe Leu Ala
            900                 905                 910

Glu Asp Ala Leu Asn Thr Val
            915

<210> SEQ ID NO 3
<211> LENGTH: 913
<212> TYPE: PRT
<213> ORGANISM: Homo sapiens

<400> SEQUENCE: 3

Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175
```

```
Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
    370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
            420                 425                 430

Ile Ile Ala Leu Met Leu Trp Arg Leu His Trp Arg Arg Leu Leu Ser
        435                 440                 445

Lys Ala Glu Arg Arg Val Leu Glu Glu Glu Leu Thr Val His Leu Ser
    450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Leu Leu Leu Ser Asn Pro Ala
            500                 505                 510

Tyr Arg Leu Leu Leu Ala Thr Tyr Ala Arg Pro Pro Arg Gly Pro Gly
        515                 520                 525

Pro Pro Thr Pro Ala Trp Ala Lys Pro Thr Asn Thr Gln Ala Tyr Ser
    530                 535                 540

Gly Asp Tyr Met Glu Pro Glu Lys Pro Gly Ala Pro Leu Leu Pro Pro
545                 550                 555                 560

Pro Pro Gln Asn Ser Val Pro His Tyr Ala Glu Ala Asp Ile Val Thr
                565                 570                 575

Leu Gln Gly Val Thr Gly Gly Asn Thr Tyr Ala Val Pro Ala Leu Pro
            580                 585                 590

Pro Gly Ala Val Gly Asp Gly Pro Pro Arg Val Asp Phe Pro Arg Ser
        595                 600                 605
```

```
Arg Leu Arg Phe Lys Glu Lys Leu Gly Glu Gly Gln Phe Gly Glu Val
    610                 615                 620

His Leu Cys Glu Val Asp Ser Pro Gln Asp Leu Val Ser Leu Asp Phe
625                 630                 635                 640

Pro Leu Asn Val Arg Lys Gly His Pro Leu Leu Val Ala Val Lys Ile
                645                 650                 655

Leu Arg Pro Asp Ala Thr Lys Asn Ala Arg Asn Asp Phe Leu Lys Glu
            660                 665                 670

Val Lys Ile Met Ser Arg Leu Lys Asp Pro Asn Ile Ile Arg Leu Leu
        675                 680                 685

Gly Val Cys Val Gln Asp Asp Pro Leu Cys Met Ile Thr Asp Tyr Met
    690                 695                 700

Glu Asn Gly Asp Leu Asn Gln Phe Leu Ser Ala His Gln Leu Glu Asp
705                 710                 715                 720

Lys Ala Ala Glu Gly Ala Pro Gly Asp Gly Gln Ala Ala Gln Gly Pro
                725                 730                 735

Thr Ile Ser Tyr Pro Met Leu Leu His Val Ala Ala Gln Ile Ala Ser
            740                 745                 750

Gly Met Arg Tyr Leu Ala Thr Leu Asn Phe Val His Arg Asp Leu Ala
        755                 760                 765

Thr Arg Asn Cys Leu Val Gly Glu Asn Phe Thr Ile Lys Ile Ala Asp
    770                 775                 780

Phe Gly Met Ser Arg Asn Leu Tyr Ala Gly Asp Tyr Tyr Arg Val Gln
785                 790                 795                 800

Gly Arg Ala Val Leu Pro Ile Arg Trp Met Ala Trp Glu Cys Ile Leu
                805                 810                 815

Met Gly Lys Phe Thr Thr Ala Ser Asp Val Trp Ala Phe Gly Val Thr
            820                 825                 830

Leu Trp Glu Val Leu Met Leu Cys Arg Ala Gln Pro Phe Gly Gln Leu
        835                 840                 845

Thr Asp Glu Gln Val Ile Glu Asn Ala Gly Glu Phe Phe Arg Asp Gln
    850                 855                 860

Gly Arg Gln Val Tyr Leu Ser Arg Pro Pro Ala Cys Pro Gln Gly Leu
865                 870                 875                 880

Tyr Glu Leu Met Leu Arg Cys Trp Ser Arg Glu Ser Glu Gln Arg Pro
                885                 890                 895

Pro Phe Ser Gln Leu His Arg Phe Leu Ala Glu Asp Ala Leu Asn Thr
            900                 905                 910

Val

<210> SEQ ID NO 4
<211> LENGTH: 911
<212> TYPE: PRT
<213> ORGANISM: Mus musculus

<400> SEQUENCE: 4

Met Gly Thr Gly Thr Leu Ser Ser Leu Leu Leu Leu Leu Leu Leu Val
1               5                   10                  15

Thr Ile Gly Asp Ala Asp Met Lys Gly His Phe Asp Pro Ala Lys Cys
            20                  25                  30

Arg Tyr Ala Leu Gly Met Gln Asp Arg Thr Ile Pro Asp Ser Asp Ile
        35                  40                  45

Ser Val Ser Ser Ser Trp Ser Asp Ser Thr Ala Ala Arg His Ser Arg
    50                  55                  60
```

```
Leu Glu Ser Ser Asp Gly Asp Gly Ala Trp Cys Pro Ala Gly Pro Val
 65                  70                  75                  80

Phe Pro Lys Glu Glu Tyr Leu Gln Val Asp Leu Arg Arg Leu His
                 85                  90                  95

Leu Val Ala Leu Val Gly Thr Gln Gly Arg His Ala Gly Gly Leu Gly
            100                 105                 110

Lys Glu Phe Ser Arg Ser Tyr Arg Leu Arg Tyr Ser Arg Asp Gly Arg
        115                 120                 125

Arg Trp Met Asp Trp Lys Asp Arg Trp Gly Gln Glu Val Ile Ser Gly
    130                 135                 140

Asn Glu Asp Pro Gly Gly Val Val Leu Lys Asp Leu Gly Pro Pro Met
145                 150                 155                 160

Val Ala Arg Leu Val Arg Phe Tyr Pro Arg Ala Asp Arg Val Met Ser
                165                 170                 175

Val Cys Leu Arg Val Glu Leu Tyr Gly Cys Leu Trp Arg Asp Gly Leu
            180                 185                 190

Leu Ser Tyr Thr Ala Pro Val Gly Gln Thr Met Gln Leu Ser Glu Val
        195                 200                 205

Met Val His Leu Asn Asp Ser Thr Tyr Asp Gly Tyr Thr Ala Gly Gly
    210                 215                 220

Leu Gln Tyr Gly Gly Leu Gly Gln Leu Ala Asp Gly Val Val Gly Leu
225                 230                 235                 240

Asp Asp Phe Arg Gln Ser Gln Glu Leu Arg Val Trp Pro Gly Tyr Asp
                245                 250                 255

Tyr Val Gly Trp Ser Asn Gln Ser Phe Pro Thr Gly Tyr Val Glu Met
            260                 265                 270

Glu Phe Glu Phe Asp Arg Leu Arg Thr Phe Gln Thr Met Gln Val His
        275                 280                 285

Cys Asn Asn Met His Thr Leu Gly Ala Arg Leu Pro Gly Gly Val Glu
    290                 295                 300

Cys Arg Phe Lys Arg Gly Pro Ala Met Ala Trp Glu Gly Glu Pro Val
305                 310                 315                 320

Arg His Ala Leu Gly Gly Ser Leu Gly Asp Pro Arg Ala Arg Ala Ile
                325                 330                 335

Ser Val Pro Leu Gly Gly His Val Gly Arg Phe Leu Gln Cys Arg Phe
            340                 345                 350

Leu Phe Ala Gly Pro Trp Leu Leu Phe Ser Glu Ile Ser Phe Ile Ser
        355                 360                 365

Asp Val Val Asn Asp Ser Ser Asp Thr Phe Pro Pro Ala Pro Trp Trp
    370                 375                 380

Pro Pro Gly Pro Pro Thr Asn Phe Ser Ser Leu Glu Leu Glu Pro
385                 390                 395                 400

Arg Gly Gln Gln Pro Val Ala Lys Ala Glu Gly Ser Pro Thr Ala Ile
                405                 410                 415

Leu Ile Gly Cys Leu Val Ala Ile Ile Leu Leu Leu Leu Ile Ile
            420                 425                 430

Ala Leu Met Leu Trp Arg Leu His Trp Arg Arg Leu Leu Ser Lys Ala
        435                 440                 445

Glu Arg Arg Val Leu Glu Glu Glu Leu Thr Val His Leu Ser Val Pro
    450                 455                 460

Gly Asp Thr Ile Leu Ile Asn Asn Arg Pro Gly Pro Arg Glu Pro Pro
465                 470                 475                 480

Pro Tyr Gln Glu Pro Arg Pro Arg Gly Thr Pro Pro His Ser Ala Pro
                485                 490                 495
```

```
Cys Val Pro Asn Gly Ser Ala Leu Leu Leu Ser Asn Pro Ala Tyr Arg
            500                 505                 510

Leu Leu Leu Ala Thr Tyr Ala Arg Pro Pro Arg Gly Pro Gly Pro Pro
            515                 520                 525

Thr Pro Ala Trp Ala Lys Pro Thr Asn Thr Gln Ala Cys Ser Gly Asp
            530                 535                 540

Tyr Met Glu Pro Glu Lys Pro Gly Ala Pro Leu Leu Pro Pro Pro Pro
545                 550                 555                 560

Gln Asn Ser Val Pro His Tyr Ala Glu Ala Asp Ile Val Thr Leu Gln
                565                 570                 575

Gly Val Thr Gly Gly Asn Thr Tyr Ala Val Pro Ala Leu Pro Pro Gly
            580                 585                 590

Ala Val Gly Asp Gly Pro Pro Arg Val Asp Phe Pro Arg Ser Arg Leu
            595                 600                 605

Arg Phe Lys Glu Lys Leu Gly Glu Gly Gln Phe Gly Glu Val His Leu
            610                 615                 620

Cys Glu Val Glu Asp Pro Gln Asp Leu Val Ser Ser Asp Phe Pro Ile
625                 630                 635                 640

Ser Val His Lys Gly His Pro Leu Leu Val Ala Val Lys Ile Leu Arg
                645                 650                 655

Pro Asp Ala Thr Lys Asn Ala Arg Asn Asp Phe Leu Lys Glu Val Lys
            660                 665                 670

Ile Met Ser Arg Leu Lys Asp Pro Asn Ile Ile Arg Leu Leu Gly Val
            675                 680                 685

Cys Val Gln Asp Asp Pro Leu Cys Met Ile Thr Asp Tyr Met Glu Asn
            690                 695                 700

Gly Asp Leu Asn Gln Phe Leu Ser Ala Arg Gln Leu Glu Asn Lys Ala
705                 710                 715                 720

Thr Gln Gly Leu Ser Gly Asp Thr Glu Ser Asp Gln Gly Pro Thr Ile
                725                 730                 735

Ser Tyr Pro Met Leu Leu His Val Gly Ala Gln Ile Ala Ser Gly Met
            740                 745                 750

Arg Tyr Leu Ala Thr Leu Asn Phe Val His Arg Asp Leu Ala Thr Arg
            755                 760                 765

Asn Cys Leu Val Gly Glu Asn Phe Thr Ile Lys Ile Ala Asp Phe Gly
            770                 775                 780

Met Ser Arg Asn Leu Tyr Ala Gly Asp Tyr Tyr Arg Val Gln Gly Arg
785                 790                 795                 800

Ala Val Leu Pro Ile Arg Trp Met Ala Trp Glu Cys Ile Leu Met Gly
                805                 810                 815

Lys Phe Thr Thr Ala Ser Asp Val Trp Ala Phe Gly Val Thr Leu Trp
            820                 825                 830

Glu Val Leu Met Leu Cys Arg Ser Gln Pro Phe Gly Gln Leu Thr Asp
            835                 840                 845

Glu Gln Val Ile Glu Asn Ala Gly Glu Phe Phe Arg Asp Gln Gly Arg
            850                 855                 860

Gln Val Tyr Leu Ser Arg Pro Pro Ala Cys Pro Gln Thr Leu Tyr Glu
865                 870                 875                 880

Leu Met Leu Arg Cys Trp Ser Arg Glu Pro Glu Gln Arg Pro Pro Phe
                885                 890                 895

Ala Gln Leu His Arg Phe Leu Ala Asp Asp Ala Leu Asn Thr Val
            900                 905                 910
```

```
<210> SEQ ID NO 5
<211> LENGTH: 874
<212> TYPE: PRT
<213> ORGANISM: Mus musculus

<400> SEQUENCE: 5

Met Gly Thr Gly Thr Leu Ser Ser Leu Leu Leu Leu Leu Leu Leu Val
1               5                   10                  15

Thr Ile Gly Asp Ala Asp Met Lys Gly His Phe Asp Pro Ala Lys Cys
            20                  25                  30

Arg Tyr Ala Leu Gly Met Gln Asp Arg Thr Ile Pro Asp Ser Asp Ile
        35                  40                  45

Ser Val Ser Ser Ser Trp Ser Asp Ser Thr Ala Ala Arg His Ser Arg
    50                  55                  60

Leu Glu Ser Ser Asp Gly Asp Gly Ala Trp Cys Pro Ala Gly Pro Val
65                  70                  75                  80

Phe Pro Lys Glu Glu Glu Tyr Leu Gln Val Asp Leu Arg Arg Leu His
                85                  90                  95

Leu Val Ala Leu Val Gly Thr Gln Gly Arg His Ala Gly Gly Leu Gly
            100                 105                 110

Lys Glu Phe Ser Arg Ser Tyr Arg Leu Arg Tyr Ser Arg Asp Gly Arg
        115                 120                 125

Arg Trp Met Asp Trp Lys Asp Arg Trp Gly Gln Glu Val Ile Ser Gly
    130                 135                 140

Asn Glu Asp Pro Gly Gly Val Val Leu Lys Asp Leu Gly Pro Pro Met
145                 150                 155                 160

Val Ala Arg Leu Val Arg Phe Tyr Pro Arg Ala Asp Arg Val Met Ser
                165                 170                 175

Val Cys Leu Arg Val Glu Leu Tyr Gly Cys Leu Trp Arg Asp Gly Leu
            180                 185                 190

Leu Ser Tyr Thr Ala Pro Val Gly Gln Thr Met Gln Leu Ser Glu Val
        195                 200                 205

Met Val His Leu Asn Asp Ser Thr Tyr Asp Gly Tyr Thr Ala Gly Gly
    210                 215                 220

Leu Gln Tyr Gly Gly Leu Gly Gln Leu Ala Asp Gly Val Val Gly Leu
225                 230                 235                 240

Asp Asp Phe Arg Gln Ser Gln Glu Leu Arg Val Trp Pro Gly Tyr Asp
                245                 250                 255

Tyr Val Gly Trp Ser Asn Gln Ser Phe Pro Thr Gly Tyr Val Glu Met
            260                 265                 270

Glu Phe Glu Phe Asp Arg Leu Arg Thr Phe Gln Thr Met Gln Val His
        275                 280                 285

Cys Asn Asn Met His Thr Leu Gly Ala Arg Leu Pro Gly Gly Val Glu
    290                 295                 300

Cys Arg Phe Lys Arg Gly Pro Ala Met Ala Trp Glu Gly Glu Pro Val
305                 310                 315                 320

Arg His Ala Leu Gly Gly Ser Leu Gly Asp Pro Arg Ala Arg Ala Ile
                325                 330                 335

Ser Val Pro Leu Gly Gly His Val Gly Arg Phe Leu Gln Cys Arg Phe
            340                 345                 350

Leu Phe Ala Gly Pro Trp Leu Leu Phe Ser Glu Ile Ser Phe Ile Ser
        355                 360                 365

Asp Val Val Asn Asp Ser Ser Asp Thr Phe Pro Pro Ala Pro Trp Trp
    370                 375                 380

Pro Pro Gly Pro Pro Pro Thr Asn Phe Ser Ser Leu Glu Leu Glu Pro
```

-continued

```
            385                 390                 395                 400
        Arg Gly Gln Gln Pro Val Ala Lys Ala Glu Gly Ser Pro Thr Ala Ile
                        405                 410                 415
        Leu Ile Gly Cys Leu Val Ala Ile Ile Leu Leu Leu Leu Leu Ile Ile
                        420                 425                 430
        Ala Leu Met Leu Trp Arg Leu His Trp Arg Arg Leu Leu Ser Lys Ala
                        435                 440                 445
        Glu Arg Arg Val Leu Glu Glu Leu Thr Val His Leu Ser Val Pro
            450                 455                 460
        Gly Asp Thr Ile Leu Ile Asn Asn Arg Pro Gly Pro Arg Glu Pro Pro
        465                 470                 475                 480
        Pro Tyr Gln Glu Pro Arg Pro Arg Gly Thr Pro Pro His Ser Ala Pro
                        485                 490                 495
        Cys Val Pro Asn Gly Ser Ala Cys Ser Gly Asp Tyr Met Glu Pro Glu
                        500                 505                 510
        Lys Pro Gly Ala Pro Leu Leu Pro Pro Pro Gln Asn Ser Val Pro
                        515                 520                 525
        His Tyr Ala Glu Ala Asp Ile Val Thr Leu Gln Gly Val Thr Gly Gly
            530                 535                 540
        Asn Thr Tyr Ala Val Pro Ala Leu Pro Pro Gly Ala Val Gly Asp Gly
        545                 550                 555                 560
        Pro Pro Arg Val Asp Phe Pro Arg Ser Arg Leu Arg Phe Lys Glu Lys
                        565                 570                 575
        Leu Gly Glu Gly Gln Phe Gly Glu Val His Leu Cys Glu Val Glu Asp
                        580                 585                 590
        Pro Gln Asp Leu Val Ser Ser Asp Phe Pro Ile Ser Val His Lys Gly
                        595                 600                 605
        His Pro Leu Leu Val Ala Val Lys Ile Leu Arg Pro Asp Ala Thr Lys
            610                 615                 620
        Asn Ala Arg Asn Asp Phe Leu Lys Glu Val Lys Ile Met Ser Arg Leu
        625                 630                 635                 640
        Lys Asp Pro Asn Ile Ile Arg Leu Leu Gly Val Cys Val Gln Asp Asp
                        645                 650                 655
        Pro Leu Cys Met Ile Thr Asp Tyr Met Glu Asn Gly Asp Leu Asn Gln
                        660                 665                 670
        Phe Leu Ser Ala Arg Gln Leu Glu Asn Lys Ala Thr Gln Gly Leu Ser
                        675                 680                 685
        Gly Asp Thr Glu Ser Asp Gln Gly Pro Thr Ile Ser Tyr Pro Met Leu
            690                 695                 700
        Leu His Val Gly Ala Gln Ile Ala Ser Gly Met Arg Tyr Leu Ala Thr
        705                 710                 715                 720
        Leu Asn Phe Val His Arg Asp Leu Ala Thr Arg Asn Cys Leu Val Gly
                        725                 730                 735
        Glu Asn Phe Thr Ile Lys Ile Ala Asp Phe Gly Met Ser Arg Asn Leu
                        740                 745                 750
        Tyr Ala Gly Asp Tyr Tyr Arg Val Gln Gly Arg Ala Val Leu Pro Ile
                        755                 760                 765
        Arg Trp Met Ala Trp Glu Cys Ile Leu Met Gly Lys Phe Thr Thr Ala
                        770                 775                 780
        Ser Asp Val Trp Ala Phe Gly Val Thr Leu Trp Glu Val Leu Met Leu
        785                 790                 795                 800
        Cys Arg Ser Gln Pro Phe Gly Gln Leu Thr Asp Glu Gln Val Ile Glu
                        805                 810                 815
```

```
Asn Ala Gly Glu Phe Phe Arg Asp Gln Gly Arg Gln Val Tyr Leu Ser
            820             825             830

Arg Pro Pro Ala Cys Pro Gln Thr Leu Tyr Glu Leu Met Leu Arg Cys
            835             840             845

Trp Ser Arg Glu Pro Glu Gln Arg Pro Pro Phe Ala Gln Leu His Arg
        850             855             860

Phe Leu Ala Asp Asp Ala Leu Asn Thr Val
865                 870
```